US006809181B2

(12) United States Patent
McCray, Jr. et al.

(10) Patent No.: US 6,809,181 B2
(45) Date of Patent: Oct. 26, 2004

(54) HUMAN BETA-DEFENSIN-3 (HBD-3), A HIGHLY CATIONIC BETA-DEFENSIN ANTIMICROBIAL PEPTIDE

(75) Inventors: Paul B. McCray, Jr., Iowa City, IA (US); Brian F. Tack, Iowa City, IA (US); Hong Peng Jia, Iowa City, IA (US); Brian C. Schutte, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 265 days.

(21) Appl. No.: 09/872,852

(22) Filed: Jun. 1, 2001

(65) Prior Publication Data

US 2002/0115602 A1 Aug. 22, 2002

Related U.S. Application Data

(60) Provisional application No. 60/208,792, filed on Jun. 1, 2000.

(51) Int. Cl.[7] .................................................. C07K 1/00
(52) U.S. Cl. ........................ 530/350; 530/350; 530/300; 435/7.1; 435/252.1; 435/320.1; 435/325; 435/455; 435/471; 514/2; 514/12
(58) Field of Search ................................. 530/350, 300; 514/12, 2; 435/7.1, 252.1, 320.1, 325, 455, 471

(56) References Cited

U.S. PATENT DOCUMENTS

6,399,370 B1    6/2002   Wilson et al. .............. 435/325

FOREIGN PATENT DOCUMENTS

| DE | 10033505.5 | | 7/2000 |
|---|---|---|---|
| WO | WO 99/13080 | * | 3/1999 |
| WO | WO 00/46245 | | 8/2000 |
| WO | WO 02/04487 | | 1/2002 |
| WO | WO 02/09738 | | 2/2002 |

OTHER PUBLICATIONS

Mathews et al., "Production of β–defensin antimicrobial peptides by the oral mucosa and slivary glands," *Infect Immun.*, 67(6):2740–2745, 1999.
Nilsson et al., "Patient education for adults with chronic eczema," *Dermatol Nurs*, 11(2):117–122, 1999.
Oren and Shai, "Mode of action of linear amphipathic α–helical antimicrobial peptides," *Biopolymers*, 47:451–463, 1998.
Osterhoff et al., "Molecular Cloning and characterization of a novel human sperm antigen (HE2) specifically expressed in the proximal epididymis," *Biol. Repod*, 50:516–525, 1994.

Russell et al., "Coordinate induction of two antibiotic genes in tracheal epithelial cells exposed to the inflammatory mediators lipopolysaccharide and tumor necrosis factor alpha," *Infect Immun.*, 64(5):1565–1568, 1996.
Singh et al., "Production of β–defensins by human airway epithelia," *Proc. Natl. Acad. Sci USA.*, 95:14961–14966, 1998.
Gallo, et al., "Antimicrobial peptides: ab emerging concept in cutaneous biology," *J. Invest Dermatol*, 111(5):739–743, 1998.
Ganz and Lehrer, "Antimicrobial peptides of vertebrates," *Current Opinions Immun*, 10:41–44, 1998.
Hamil et al., "HE2β and HE2γ, new members of an epididymis–specific family of androgen–regulated proteins in the human," *Endocrinology*, 141(3):1245–1253, 2000.
Harder et al., "Short communication—Mapping of the gene encoding human β–Defensin–2 (DEFB2) to chromosome region 8p22–p23.1," *Genomics*, 46:472–475, 1997.
Jia et al., "Discovery of new human β–defensins using a genomics–based approach," *Gene*, 263:211–218, 2001.
Kirchhoff et al., :CD52 mRNA is modulated by androgens and temperature in epididymal cell cultures, *Mol. Reprod. Dev.*, 56:26–33, 2000.
Krull et al., "Region–specific variation of gene expression in the human epididymis as revealed by in situ hybridization with tissue–specific cDNAs," *Mol. Reprod. Dev.*, 34:16–24, 1993.
Liu et al., "Induction of apoptosis by thiuramdisulfides, the reactive metabolites of dithiocarbamates, through coordinative modulation of NFκB, c–fos/c–jun, and p53 proteins," *Mol. Carcinog.*, 22:235–246, 1998.
Co–pending U.S. patent application Ser. No. 09/642,744 by Brian F. Tack et al., filed Aug. 18, 2000.

* cited by examiner

Primary Examiner—Karen Cochrane Carlson
Assistant Examiner—Hope A. Robinson
(74) Attorney, Agent, or Firm—Fulbright & Jaworski

(57) ABSTRACT

The present invention relates a novel antimicrobial peptide HBD-3 and derivatives thereof as well as the gene encoding the peptide. The invention further relates to methods of use of the HBD-3 peptide including a method of inhibiting microbial growth by administering an effective amount of the HBD-3 peptide alone or in combinination with other antimicrobial agents or antibiotics. In addition, the immunomodulatory properties of the HBD-3 peptide also facilitate the manipulation of the immune response, i.e., as a chemoattractant for immature dentritic cells or memory T cells.

9 Claims, 5 Drawing Sheets

FETAL LUNG  GINGIVAL EPITHELIUM

IL-1β   -   +           -   +

GAPDH

HBD-3

RT   -   +   -   +        -   +   -   +

PLACENTA MEMBRANE   ESOPHAGUS   TRACHEA

GAPDH

HBD-3

SEQUENCE LISTING

<160> NUMBER OF SEQ ID NOS: 24

<210> SEQ ID NO 1
<211> LENGTH: 204
<212> TYPE: DNA
<213> ORGANISM: Homo sapiens

<400> SEQUENCE: 1

```
atgaggatcc attatcttct gtttgctttg ctcttcctgt ttttggtgcc tgttccaggt      60
catggaggaa tcataaacac attacagaaa tattattgca gagtcagagg cggccggtgt     120
gctgtgctca gctgccttcc aaaggaggaa cagatcggca agtgctcgac gcgtggccga     180
aaatgctgcc gaagaaagaa ataa                                             204
```

<210> SEQ ID NO 2
<211> LENGTH: 67
<212> TYPE: PRT

```
<213> ORGANISM: Artificial Sequence
<220> FEATURE:
<223> OTHER INFORMATION: Description of Artificial Sequence: Synthetic
      Peptide

<400> SEQUENCE: 2

Met Arg Ile His Tyr Leu Leu Phe Ala Leu Leu Phe Leu Phe Leu Val
1               5                   10                  15

Pro Val Pro Gly His Gly Gly Ile Ile Asn Thr Leu Gln Lys Tyr Tyr
            20                  25                  30

Cys Arg Val Arg Gly Gly Arg Cys Ala Val Leu Ser Cys Leu Pro Lys
        35                  40                  45

Glu Glu Gln Ile Gly Lys Cys Ser Thr Arg Gly Arg Lys Cys Cys Arg
    50                  55                  60

Arg Lys Lys
65

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Thr Leu Gln Lys Tyr Tyr Cys Arg Val Arg Gly Gly Arg Cys Ala Val
1               5                   10                  15

Leu Ser Cys Leu Pro Lys Glu Glu Gln Ile Gly Lys Cys Ser Thr Arg
            20                  25                  30

Gly Arg Lys Cys Cys Arg Arg Lys Lys
        35                  40

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
            20                  25                  30

Cys Ser Thr Arg Gly Arg Lys Cys Cys Arg Arg Lys Lys
        35                  40                  45

<210> SEQ ID NO 5
<211> LENGTH: 20
<212> TYPE: DNA
<213> ORGANISM: Homo sapiens

<400> SEQUENCE: 5
atgaggatcc attatcttct                                                 20

<210> SEQ ID NO 6
<211> LENGTH: 20
<212> TYPE: DNA
<213> ORGANISM: Homo sapiens

<400> SEQUENCE: 6
```

```
ttatttcttt cttcggcagc                                        20

<210> SEQ ID NO 7
<211> LENGTH: 20
<212> TYPE: DNA
<213> ORGANISM: Homo sapiens

<400> SEQUENCE: 7
tgtttgcttt gctcttcctg                                        20

<210> SEQ ID NO 8
<211> LENGTH: 20
<212> TYPE: DNA
<213> ORGANISM: Homo sapiens

<400> SEQUENCE: 8
ctttcttcgg cagcattttc                                        20

<210> SEQ ID NO 9
<211> LENGTH: 20
<212> TYPE: DNA
<213> ORGANISM: Homo sapiens

<400> SEQUENCE: 9
gtcagtggtg gacctgacct                                        20

<210> SEQ ID NO 10
<211> LENGTH: 20
<212> TYPE: DNA
<213> ORGANISM: Homo sapiens

<400> SEQUENCE: 10
aggggtctac atggcaactg                                        20

<210> SEQ ID NO 11
<211> LENGTH: 20
<212> TYPE: DNA
<213> ORGANISM: Homo sapiens

<400> SEQUENCE: 11
tcggagaact cagggaaaga                                        20

<210> SEQ ID NO 12
<211> LENGTH: 20
<212> TYPE: DNA
<213> ORGANISM: Homo sapiens

<400> SEQUENCE: 12
gcccttggga tacttcaaca                                        20

<210> SEQ ID NO 13
<211> LENGTH: 28
<212> TYPE: DNA
<213> ORGANISM: Homo sapiens

<400> SEQUENCE: 13
tgttccaggt aagatgggct gggaaatc                               28

<210> SEQ ID NO 14
<211> LENGTH: 28
<212> TYPE: DNA
<213> ORGANISM: Homo sapiens
```

-continued

```
<400> SEQUENCE: 14
gtgctgtttt gtcattgcag gtcatgga                                28

<210> SEQ ID NO 15
<211> LENGTH: 28
<212> TYPE: DNA
<213> ORGANISM: Homo sapiens

<400> SEQUENCE: 15
gtttccaggt aaatggaaa ggtgaccc                                 28

<210> SEQ ID NO 16
<211> LENGTH: 28
<212> TYPE: DNA
<213> ORGANISM: Homo sapiens

<400> SEQUENCE: 16
gtgtgtttcc acttgcacag gatcgtct                                28

<210> SEQ ID NO 17
<211> LENGTH: 28
<212> TYPE: DNA
<213> ORGANISM: Homo sapiens

<400> SEQUENCE: 17
ttaccaaggt gagtcaggga ccaacacg                                28

<210> SEQ ID NO 18
<211> LENGTH: 28
<212> TYPE: DNA
<213> ORGANISM: Homo sapiens

<400> SEQUENCE: 18 ctcccttgt ttccttctag tgcacatc                                 28

<210> SEQ ID NO 19
<211> LENGTH: 28
<212> TYPE: DNA
<213> ORGANISM: Homo sapiens

<400> SEQUENCE: 19
tgggccaggt gagcattcat aaaacaca                                28

<210> SEQ ID NO 20
<211> LENGTH: 28
<212> TYPE: DNA
<213> ORGANISM: Homo sapiens

<400> SEQUENCE: 20
ctcttctgtt gtatccatag gggatgtt                                28

<210> SEQ ID NO 21
<211> LENGTH: 28
<212> TYPE: DNA
<213> ORGANISM: Homo sapiens

<400> SEQUENCE: 21
ccattctggt gagaaaaagc gtgacatt                                28

<210> SEQ ID NO 22
<211> LENGTH: 28
<212> TYPE: DNA
<213> ORGANISM: Homo sapiens
```

```
<400> SEQUENCE: 22
tttggcctca tgttcctcag aaatgaaa                                              28

<210> SEQ ID NO 23
<211> LENGTH: 28
<212> TYPE: DNA
<213> ORGANISM: Homo sapiens

<400> SEQUENCE: 23
tccaccaggt gagatgggga ggatggga                                              28

<210> SEQ ID NO 24
<211> LENGTH: 28
<212> TYPE: DNA
<213> ORGANISM: Homo sapiens

<400> SEQUENCE: 24
ctgctcttat ttgggaacag ggacaggc                                              28
```

HUMAN BETA-DEFENSIN-3 (HBD-3), A HIGHLY CATIONIC BETA-DEFENSIN ANTIMICROBIAL PEPTIDE

This application claims benefit of the filing date of U.S. Provisional Patent Application Ser. No.60/208,792 filed on Jun. 1, 2000 which is incorporated by reference herein.

The government owns rights in the present invention pursuant to grant number HL-61234-01 from the National Institutes of Health.

BACKGROUND OF THE INVENTION

1. Field of the Invention

This invention relates generally to an antimicrobial agent and to methods of preventing microbial growth. In particular, the present invention involves compositions comprising an antimicrobial peptide and methods for its use.

2. Description of Related Art

The first antibiotics were used clinically in the 1940s and 1950s, and their use has been increasing significantly since this period. Although an invaluable advance, antibiotic and antimicrobial therapy suffers from several problems, particularly when strains of various bacteria appear that are resistant to antibiotics. Interestingly, bacteria resistant to streptomycin were isolated about a year after this antibiotic was introduced.

The development of antibiotic resistance is a serious and life-threatening event of worldwide importance. For example, strains of *Staphylococcus* are known that are immune to all antibiotics except one (Travis, 1994). Such bacteria often cause fatal hospital infections. Among other drug resistant organisms are: *pneumococci* that cause pneumonia and meningitis; Cryptosporidium and *E. coli* that cause diarrhea; and enterococci that cause blood-stream, surgical wound and urinary tract infections (Berkelman et. al., 1994). The danger is further compounded by the fact that antibiotic and antimicrobial resistance may be spread vertically and horizontally by plasmids and transposons.

Davies (1986) described seven basic biochemical mechanisms for naturally-occurring antibiotic resistance: (1) alteration (inactivation) of the antibiotic; (2) alteration of the target site; (3) blockage in the transport of the antibiotic; (4) by-pass of the antibiotic sensitive-step (replacement); (5) increase in the level of the inhibited enzyme (titration of drug); (6) sparing the antibiotic-sensitive step by endogenous or exogenous product; and (7) production of a metabolite that antagonizes action of inhibitor.

Antimicrobial peptides have been isolated from plants, insects, fish, amphibia, birds, and mammals (Gallo, 1998; Ganz & Lehrer, 1998). Vertebrate skin, trachea and tongue epithelia are rich sources of these peptides, which may explain the unexpected resistance of these tissues to infection (Russell et al. 1996). Although previously considered an evolutionarily primitive system of immune protection with little relevance beyond minimal antimicrobial activity, it has subsequently been determined that antimicrobial peptides are a primary component of an innate immune response and are expressed by mammalian cells during inflammatory events such as wound repair, contact dermatitis and psoriasis (Nilsson, 1999). The efficacy of antimicrobial peptides is based upon their ability to create pores in the cytoplasmic membrane of microorganisms (Oren et al., 1998). They also have been shown to stimulate syndecan expression, chemotaxis, and chloride secretion (Gallo, 1998).

The present invention seeks to employ antimicrobial compounds to overcome the deficiencies inherent in the prior art by providing new compositions, combined compositions, methods and kits, for treating infections and reducing resistance to antimicrobials and antibiotics.

SUMMARY OF THE INVENTION

The instant inventions seeks to overcome the noted deficiencies in the art by disclosing the previously unidentified antimicrobial peptide human beta-defensin-3 (HBD-3). The instant application provides the peptide and nucleic acid sequences for HBD-3 as well as methods of use for each.

As noted, the instant invention relates the peptide sequence of HD-3. A preferred embodiment of the instant invention is therefore an isolated antimicrobial peptide comprising the amino acid sequence: MRIHYLLFALL-FLFLVPVPGHGGIINTLQKYYCRVRGGR-CAVLSCLPKEEQIGKCSTRGRKCCRRKK (SEQ ID NO: 2). In an alternate embodiment of the invention, the HBD-3 peptide may be utilized in its functional state, i.e., absent the signaling sequence, and thus comprising the amino acid sequence: TLQKYYCRVRGGRCAVLSCLPKE-EQIGKCSTRGRKCCRRKK (SEQ ID NO: 3). It is contemplated that the HBD-3 peptide, as set forth may be administered to a host. For this or related purposes, the peptide may be dispersed within a pharmaceutically acceptable composition which in some aspects of the invention includes a pharmaceutically acceptable carrier. Alternate embodiments of the invention contemplate that the HBD-3 peptide, dispersed in a pharmaceutical composition may be used for, for example, topical administration, oral administration, or parenteral administration. Where HBD-3 is administered parenterally, the administration may be, for example, by injection or by inhalation.

Another aspect of the instant invention relates a beta-defensin encoding nucleic acid molecule isolated from other coding sequences where the nucleic acid molecule encodes a peptide of the amino acid sequence: MRIHYLLFALLFLFLVPVPGHGGIINTLQKYYCRVRG-GRCAVLSCLPKEEQIGKCSTRGRKCCRRKK (SEQ ID NO: 2). In a preferred embodiment of the instant invention the nucleic acid molecule encoding HBD-3 is incorporated into a vector. Where a vector is utilized, it is particularly contemplated that the vector will be an expression vector.

Additional aspects of the invention contemplate that the expressed or mature peptide of the instant invention may be used to inhibit or prevent the growth of bacteria or other microbes. A preferred embodiment of the instant invention is therefore, a method of inhibiting the growth of a microbe by introducing into an environment an antimicrobial peptide comprising the amino acid sequence of the HBD-3 peptide. Where the peptide is introduced into an environment to prevent microbial growth, it is contemplated that the peptide will be dispersed in a composition capable of sustaining the antimicrobial properties of the peptide in the environment. A preferred embodiment is thus the introduction of the peptide into an environment, for example a host organism, with the peptide dispersed in a pharmaceutical composition.

The antimicrobial peptide of the instant invention is of particular interest because it does not appear that microbial species have selectively developed resistance to its effects. It is therefore contemplated that the HBD-3 peptide will be useful in combination with other antimicrobial agents, particularly those agents to which certain microbial strains may be developing resistance. Therefore, a preferred embodiment of the instant invention is a method of introducing the HBD-3 peptide into an environment in combination with an additional antimicrobial agent. The agents may be introduced concurrently, or the HBD-3 peptide may be introduced before or after the second antimicrobial agent.

Alternate embodiments of the invention contemplate the use of a variety of second antimicrobial agents in the context of the invention. Agents of particular relevance are, for example, antimicrobial agents that are protein synthesis inhibitors, cell wall growth inhibitors, cell membrane synthesis inhibitors, nucleic acid synthesis inhibitors, or competitive inhibitors.

While the HBD-3 peptide may be dispersed into formulations for delivery into a variety of environments, it is specifically contemplated that the peptide will be useful in the prevention of microbial growth in or on a host, particularly the growth of strains that exhibit some form of drug resistant phenotype. A preferred embodiment of the instant invention is therefore a method of inhibiting growth of a microbe in a host, comprising administering to the host the HBD-3 antimicrobial peptide. Alternate embodiments specifically contemplate that the HBD-3 peptide will be combined with a second antimicrobial agent, which may be administered as previously described. The second agent may comprise an antimicrobial agent exhibiting, for example, one of the following properties: protein synthesis inhibition, cell wall growth inhibition, cell membrane synthesis inhibition, nucleic acid synthesis inhibition, or competitive inhibition.

In another aspect of the invention, the HBD-3 peptide may be contained within a kit. In a preferred embodiment of the invention, the kit may further comprise an additional antimicrobial agent, for example an antimicrobial agent as previously described.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4: Amino acid sequence alignment of HBD-3 and HE2β1 with other human β-defensin peptides (HBD=human β-defensin, HE2β1=human epididymal secretory protein). Conserved amino acids are highlighted in black, conservative substitutions are noted in gray. Note the conserved six cysteine motif near the C-terminal end.

DESCRIPTION OF ILLUSTRATIVE EMBODIMENTS

Figure 1:
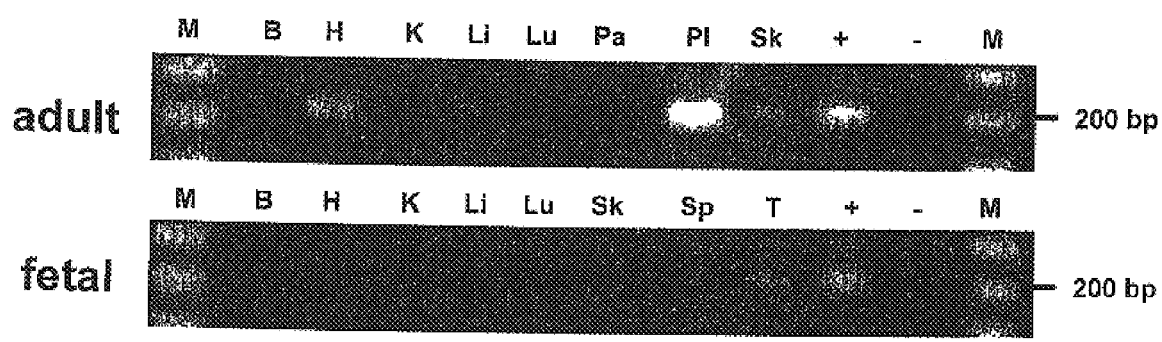
FIG. 1: PCR expression analysis of cDNA from multiple tissues.

The instant invention relates to novel compositions including human beta definsin-3 (HBD-3) and related peptides and methods for their use. The HBD-3 peptide is a highly cationic antimicrobial peptide of the beta-defensin family. The peptide exhibits antimicrobial properties similar to other related peptides and also appears to act as an immunomodulator. Evidence suggests that the peptide interacts with dendritic cells and T cells and may influence the development and progression of cellular and humoral responses. The instant invention discloses the nucleic acid encoding and amino acid sequence of the peptide and provides a variety of uses for both the peptide and its derivatives, antibodies recognizing the peptide and the nucleic acid sequence encoding the peptide. The functional gene (SEQ ID NO: 1) encodes a peptide of 67 amino acids as set forth in SEQ ID NO: 2:

MRIHYLLFALLFLFLVPVPGHGGIINTLQKYY-CRVRGGRCAVLSCLPKEEQIGKCSTRGRKCCRRKK (SEQ ID NO: 2).

It is hypothesized that the signal sequence is cleaved from the 67 residue peptide to produce a mature peptide of 41–45 residues, as set forth in SEQ ID NO: 3 or SEQ ID NO: 4: TLQKYYCRVRGGRCAVLSCLPKEEQIGKCSTR-GRKCCRRKK (SEQ ID NO: 3) GIINTLQKYYCRVRGGRCAVLSCLPKEEQIGKCS-TRGRKCCRRKK (SEQ ID NO: 4).

The antimicrobial properties of HBD-3 are an important aspect of the instant invention. Pathogenic microbial strains increasingly exhibit resistance or decreased sensitivity to commercially available antibiotics and antimicrobials. While microbial strains have acquired resistance to many commercial antibiotics within a few decades, it does not appear that similar resistance to antimicrobial peptides has been acquired, despite thousands of years of evolution. The antimicrobial properties of HBD-3 are thus useful, alone and in combination with other antimicrobial agents, in the inhibition of microbial growth and/or infection.

A person of ordinary skill would recognize that the antimicrobial properties of the HBD-3 peptide may be exploited in a variety of applications. While preferred embodiments of the invention encompass administration of the peptide to a host for therapeutic or prophylactic benefit, it also is envisioned that the peptides will have other uses. In alternate embodiments, it is envisioned that the HBD-3 peptide may be included in antiseptic or antimicrobial preparations for application or introduction into environments in which an individual wishes to prevent or suppress microbial growth. Thus, for example, in one aspect of the instant invention, the HBD-3 protein is diluted in a composition for application to a surface, such as a work surface or a surgical instrument, for the prevention and/or suppression of microbial growth.

Where the antimicrobial peptide is to be provided to a host, the nature of the peptide facilitates a number of alternate routes of administration. The durability of the peptide facilitates not only internal administration but also application of HBD-3 in a topical formulation. Where HBD-3 is to be given internally, a variety of means of delivery are possible. In a preferred embodiment of the invention, the peptide is diluted in a suitable pharmaceutical composition for delivery by inhalation for the treatment or prevention of pulmonary infections. It is further contemplated that the nucleic acid sequence of the peptide may be delivered to cells by an appropriate vector or DNA delivery vehicle in the context of gene therapy.

As antimicrobial peptides have been determined to be important components of the innate immune system, it is envisioned that monitoring expression of the protein in vivo may prove to be important in not only detecting latent infection but also potentially as an indicator of immune dysfunction. In each context, HBD-3 nucleic acid signal or peptide expression may be monitored by means readily known in the art.

A. Nucleic Acids

The instant invention relates to genetic sequences for specific genes expressed by immune cells and exhibiting antimicrobial activity. Therefore, the use, manipulation, detection, isolation, amplification and screening of nucleic acids are important aspects of the invention.

In the context of the instant invention, genes are sequences of DNA in an organism's genome encoding information that is converted into various products making up a whole cell. They are expressed by the process of transcription, which involves copying the sequence of DNA into RNA. Most genes encode information to make proteins, but some encode RNAs involved in other processes. If a gene encodes a protein, its transcription product is called mRNA ("messenger" RNA). After transcription in the nucleus (where DNA is located), the mRNA must be transported into the cytoplasm for the process of translation, which converts the code of the mRNA into a sequence of amino acids to form protein. In order to direct transport into the cytoplasm the 3' ends of mRNA molecules are post-transcriptionally modified by addition of several adenylate residues to form the "polyA" tail. This characteristic modification distinguishes gene expression products destined to make protein from other molecules in the cell, and thereby provides one means for detecting and monitoring the gene expression activities of a cell.

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T" and cytosine "C") or RNA (e.g., A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

Hybridization is understood to mean the forming of a double stranded molecule and/or a molecule with partial double stranded nature. Stringent conditions are those that allow hybridization between two homologous nucleic acid sequences, but precludes hybridization of random sequences. For example, hybridization at low temperature and/or high ionic strength is termed low stringency. Hybridization at high temperature and/or low ionic strength is termed high stringency. Low stringency is generally performed at 0.15 M to 0.9 M NaCl at a temperature range of 20° C. to 50° C. High stringency is generally performed at 0.02 M to 0.15 M NaCl at a temperature range of 50° C. to 70° C. It is understood that the temperature and/or ionic strength of a desired stringency are determined in part by the length of the particular probe, the length and/or base content of the target sequences, and/or to the presence of formamide, tetramethylammonium chloride and/or other solvents in the hybridization mixture. It is also understood that these ranges are mentioned by way of example only, and/or that the desired stringency for a particular hybridization reaction is often determined empirically by comparison to positive and/or negative controls.

Accordingly, the nucleotide sequences of the disclosure may be used for their ability to selectively form duplex molecules with complementary stretches of genes and/or RNA. Depending on the application envisioned, it is preferred to employ varying conditions of hybridization to achieve varying degrees of selectivity of probe towards target sequence.

Nucleic acid molecules having sequence regions consisting of contiguous nucleotide stretches of about 13, 14, 15, 16, 17, 18, 20, 25, 30, 35, 40, 45, 50, 55, 60, 70, 80, 90, 100, 125, 150, 175, 200, or 250 identical or complementary to the target DNA sequence, are particularly contemplated as hybridization probes for use in embodiments of the instant invention. It is contemplated that long contiguous sequence regions, for use in, for example, genomic screening, may be utilized including those sequences comprising about 100, 200, 300, 400, 500 or more contiguous nucleotides.

The use of a probe or primer of between 13 and 100 nucleotides, preferably between 17 and 100 nucleotides in length, or in some aspects of the invention up to 1–2 kb or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Depending on the application envisioned, one would desire to employ varying conditions of hybridization to achieve varying degrees of selectivity of the probe or primers for the target sequence. For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

For applications requiring high selectivity, it is preferred to employ relatively stringent conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe and/or the template and/or target strand, and/or would be particularly suitable for isolating specific genes and/or detecting specific mRNA transcripts. It is generally appreciated that conditions may be rendered more stringent by the addition of increasing amounts of formamide.

In the context of the instant application, nucleic acids are also important for expression systems producing the claimed peptide.

B. Peptide Production

A person of ordinary skill would be aware of a variety of means of producing, isolating, purifying and manipulating the peptide molecules set forth herein. Exemplary methods are briefly summarized below.

1. Peptide Synthesis a. Chemical Synthesis

The antimicrobial peptides of the instant invention may be chemically synthesized. An exemplary method for chemical synthesis of such a peptide is as follows. Using the solid phase peptide synthesis method of Sheppard et al (1981) an automated peptide synthesizer (Pharmacia LKB Biotechnology Co., LKB Biotynk 4170) adds N,N'-dicyclohexylcarbodiimide to amino acids whose amine functional groups are protected by 9-fluorenylmethoxycarbonyl groups, producing anhydrides of the desired amino acid (Fmoc-amino acids). An Fmoc amino acid corresponding to the C-terminal amino acid of the desired peptide is affixed to Ultrosyn A resin (Pharmacia LKB Biotechnology Co.) through its carboxyl group, using dimethylaminopyridine as a catalyst. The resin is then washed with dimethylformamide containing iperidine resulting in the removal of the protective amine group of the C-terminal amino acid. A Fmoc-amino acid anhydride corresponding to the next residue in the peptide sequence is then added to the substrate and allowed to couple with the unprotected amino acid affixed to the resin. The protective amine group is subsequently removed from the second amino acid and the above process is repeated with additional residues added to the peptide in a like manner until the sequence is completed. After the peptide is completed, the protective groups, other than the acetoamidomethyl group are removed and the peptide is released from the resin with a solvent consisting of, for example, 94% (by weight) trifluoroacetic acid, 5% phenol, and 1% ethanol. The synthesized peptide is subsequently purified using high-performance liquid chromatography or other peptide purification technique discussed below.

b. Expression Systems

The antimicrobial peptides of the instant invention may be expressed by a prokaryotic or eukaryotic expression vector. The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," ie., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202; U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 1 lists several elements/promoters that may be employed, in the context of the present invention, to regulate the expression of a gene. This list is not intended to be exhaustive of all the possible elements involved in the promotion of expression but, merely, to be exemplary thereof. Table 2 provides examples of inducible elements, which are regions of a nucleic acid sequence that can be activated in response to a specific stimulus.

TABLE 1

| Promoter and/or Enhancer | |
|---|---|
| Promoter/Enhancer | References |
| Immunoglobulin Heavy Chain | Banerji et al., 1983; Gilles et al., 1983; Grosschedl et al., 1985; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQβ | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Treisman, 1986; Deschamps et al., 1985 |
| Insulin | Edlund et al., 1985 |
| Neural Cell Adhesion Molecule (NCAM) | Hirsch et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988, Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |

TABLE 1-continued

Promoter and/or Enhancer

| Promoter/Enhancer | References |
| --- | --- |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
| --- | --- | --- |
| MT II | Phorbol Ester (TEA) Heavy metals | Palmiter et al., 1982; Haslinger et al., 1985; Searle et al., 1985; Stuart et al., 1985; Imagawa et al., 1987, Karin et al., 1987; Angel et al., 1987b; MeNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha 2 (XI) collagen (Tsumaki et al., 1998), D1A dopamine receptor gene (Lee et al., 1997), insulin-like growth factor II (Wu et al., 1997), human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message. See also U.S. Pat. Nos. 5,925,565 and 5,935,819, herein incorporated by reference.

3. Multiple Cloning Sites

Vectors can include a multiple cloning site (MCS), which is a nucleic acid region that contains multiple restriction enzyme sites, any of which can be used in conjunction with standard recombinant technology to digest the vector. See Carbonelli et al., 1999; Levenson et al.; 1998, and Cocea, 1997; incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. See Chandler et al., 1997, herein incorporated by reference.

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and Solopack™ Gold Cells (Stratagene®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

10. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MaxBac® 2.0 from Invitrogen® and BacPack™ Baculovirus Expression System From Clontech®.

Other examples of expression systems include Stratagene®'s Complete Control™ Inducible Mammalian Expression System, which involves a synthetic ecdysone-inducible receptor, or its pET Expression System, an *E. coli* expression system. Another example of an inducible expression system is available from Invitrogen®, which carries the T-Rex™ (tetracycline-regulated expression) System, an inducible mammalian expression system that uses the full-length CMV promoter. Invitrogen® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

2. Fusion Proteins

The antimicrobial peptides of the instant application may be combined with fusion partners to produce fusion proteins. It is envisioned that such constructs might include combinations of an antimicrobial peptide with a partner also exhibiting some level of antimicrobial activity. Such a construct generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification if such removal is desired. Other useful fusions include linking of functional domains, such as active sites from enzymes, glycosylation domains, cellular targeting signals or transmembrane regions.

It is envisioned that, to construct fusion proteins, the cDNA sequence encoding the antimicrobial peptide would be linked to the cDNA sequence encoding the desired fusion partner. The antimicrobial peptide sequences disclosed in this application allow for the deduction of encoding DNA. Such sequences may be prepared using conventional techniques, and used as probes to recover corresponding DNA's from genomic or cDNA libraries. Following cloning, such DNA's can then be incorporated in appropriate expression vectors and used to transform host cells (e.g., bacterial or mammalian cells), which can be cultured to form recombinant antimicrobial peptides.

3. Peptide Substitutions

As modifications and changes may be made in the structure of the HBD-3 gene and peptides or proteins of the present invention, and still obtain molecules having like or otherwise desirable characteristics, such biologically functional equivalents are also encompassed within the present invention.

It is contemplated that specific modifications may be made within the peptide that maintain the peptides antimicrobial properties of the claimed sequence, but also confers some additional desirable property to the peptide. It is well known in the art that certain amino acids may be substituted for other amino acids in a protein structure without appreciable loss of peptide activity. Since it is the interactive capacity and nature of a peptide that defines that peptide's biological functional activity, certain amino acid sequence substitutions can be made in a protein sequence (or, of course, its underlying DNA coding sequence) and nevertheless obtain a peptide with like properties. It is thus contemplated by the inventors that various changes may be made in the sequence of HBD-3 peptides, or the underlying nucleic acids, without appreciable loss of biological utility or activity and perhaps may enhance desired activities.

For example, in designing peptide constructs with antimicrobial properties, substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. Since it is the interactive capacity and nature of a protein that defines that protein's biological functional activity, certain amino acid substitutions can be made in a protein sequence, and its underlying DNA coding sequence which potentially create a peptide with superior characteristics.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Amino acid substitutions are generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

As used in this application, the term "an isolated nucleic acid encoding a antimicrobial peptide refers to a nucleic acid molecule that has been isolated free of total cellular nucleic acid. The term "functionally equivalent codon" is used herein to refer to codons that encode the same amino acid, such as the six codons for arginine or serine (Table 3, below), and also refers to codons that encode biologically equivalent amino acids, as discussed in the following pages.

TABLE 3

CODONS

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of an antimicrobial peptide gene will be sequences that encompassed by the present invention. Nucleic acid sequences of the present invention may also be functionally defined as sequences that are capable of hybridizing to a nucleic acid segment encoding an antimicrobial peptide.

The DNA segments of the present invention include those encoding biologically functional equivalent antimicrobial peptides, as described above. Functionally equivalent proteins or peptides may be created via the application of recombinant DNA technology, in which changes in the protein structure may be engineered, based on considerations of the properties of the amino acids being exchanged, or as a result of natural selection. Changes designed by man may be introduced through the application of site-directed mutagenesis techniques or may be introduced randomly and screened later for the desired function.

4. Protein Purification

Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic, immunologic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or HPLC.

Certain aspects of the present invention concern the purification, and in particular embodiments, the substantial purification, of an encoded peptide. The term "purified peptide" as used herein, is intended to refer to a composition, isolatable from other components, wherein the peptide is purified to any degree relative to its naturally-obtainable state. A purified peptide therefore also refers to a peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more peptides in the composition. The term "purified to homogeneity" is used to mean that the composition has been purified such that there is single protein species based on the particular test of purity employed for example SDS-PAGE or HPLC.

Various methods for quantifying the degree of purification of the peptide will be known to those of skill in the art in light of the present disclosure. These include, for example, assessing the amount of peptides within a fraction by SDS/PAGE analysis.

There is no general requirement that the peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is particularly contemplated that the peptides of the instant invention may be isolated, purified or visualized on denaturing and non-denaturing gels, particularly acid urea gels. Generally, cationic peptides such as beta defensins are visualized on acid urea western blots or gels where the proteins migrate according to their charge. Persons of skill in the art would be aware of these and other analogous methods, such as, for example SDS/PAGE. It is known that the migration of a peptide can vary, sometimes significantly, with different conditions of acid urea gels or SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

C. Immunological Reagents

In the context of the instant invention, it is envisioned that antibodies directed against the claimed peptides may be of relevance. Thus, for certain aspects of the invention, one or more antibodies may be produced to the expressed antimicrobial peptides. These antibodies may be used in various diagnostic, therapeutic or screening applications.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's dental disease are likewise known and such custom-tailored antibodies are also contemplated.

The methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m$^2$) (Johnson/Mead, NJ), cytokines such as γ-interferon, IL-2, or IL-12 or genes encoding proteins involved in immune helper functions, such as B7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat.

No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages, but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate.

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Alternatively, monoclonal antibody fragments encompassed by the present invention can be synthesized using an automated peptide synthesizer, or by expression of full-length gene or of gene fragments in *E. coli*.

1. Antibody Conjugates

For therapeutic, diagnostic and screening application, it is envisioned that antibodies directed to antimicrobial peptides may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limitng examples of effector molecules which have been attached to antibodies include toxins, anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti-cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody-directed imaging".

Many appropriate imaging agents are known in the art, as are methods for their attachment to antibodies (see, for e.g., U.S. Pat. Nos. 5,021,236, 4,938,948, and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^3$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850, 752; 3,939,350; 3,996,345; 4,277,437; 4,275,149 and 4,366, 241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periiodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has :Fi been reported to produce diagnostically and therapeutically promising antibodies which are currently in clinical evaluation.

2. Immunodetection Methods

In still further embodiments, the present invention concerns immunodetection methods for binding, purifying, removing, quantifying and/or otherwise generally detecting antimicrobial expressed message(s), protein(s), polypeptide (s) or peptide(s). Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager R et al., 1993, each incorporated herein by reference.

In general, the immunobinding methods include obtaining a sample suspected of containing antimicrobial peptide and contacting the sample with a first antibody directed against translated product antibody in accordance with the present invention, as the case may be, under conditions effective to allow the formation of immunocomplexes.

These methods include methods for purifying an antimicrobial peptide from organelle, cell, tissue or organism's samples. In these instances, the antibody removes the antimicrobial peptide component from a sample. The antibody will preferably be linked to a solid support, such as in the form of a column matrix, and the sample suspected of containing the ORF message, protein, polypeptide and/or peptide antigenic component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the antimicrobial peptide, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts are preferred.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antimicrobial peptide present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939, 350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antimicrobial peptide antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

In the clinical diagnosis and/or monitoring of patients with various forms a disease, such as, for example, immune dysfunction, the detection of an antimicrobial peptide, and/or an alteration in the levels of an antimicrobial peptide, in comparison to the levels in a corresponding biological sample from a normal subject is potentially indicative of a patient with cancer. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive. Of course, the antibodies of the present invention in any immunodetection or therapy known to one of ordinary skill in the art.

a. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the antimicrobial peptide antibodies of the invention are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another antimicrobial peptide antibody that is linked to a detectable label. This type of ELISA is a simple "sandwich ELISA". Detection may also be achieved by the addition of a second antimicrobial peptide antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the antimicrobial peptide antibodies of the invention. After binding and/or washing to remove non-specifically bound immune complexes, the bound antimicrobial peptide antibodies are detected. Where the initial antimicrobial peptide antibodies are linked to a detectable label, the immune complexes may be detected directly. Again, the immune complexes may be detected using a second antibody that has binding affinity for the first antimicrobial peptide antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, eg., using a visible spectra spectrophotometer.

b. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25–50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

D. Gene Therapy

In particular embodiments of the instant invention, it is envisioned that antimicrobial peptides and the nucleic acid sequence encoding them may be utilized in gene therapy. For example, individuals immunodeficient due to disease, injury or genetic defect may be administered a nucleic acid construct comprising a genetic sequence encoding the HBD-3 antimicrobial peptides.

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

1. DNA Delivery Using Viral Vectors

The ability of certain viruses to infect cells or enter cells via receptor-mediated endocytosis, and to integrate into host cell genome and express viral genes stably and efficiently have made them attractive candidates for the transfer of foreign genes into mammalian cells. Preferred gene therapy vectors of the present invention will generally be viral vectors.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

a. Adenoviral Vectors

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue-specific transforming construct that has been cloned therein.

The expression vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (E1A and E1B; Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) discloses improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1991; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993). Recombinant adenovirus and adeno-associated virus (see below) can both infect and transduce non-dividing human primary cells.

b. AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in viva. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

c. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

d. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

e. Modified Viruses

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Other Methods of DNA Delivery

In various embodiments of the invention, DNA is delivered to a cell as an expression construct. In order to effect expression of a gene construct, the expression construct must be delivered into a cell. As described herein, the preferred mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA or plasmids. Transfer of the construct may be performed by any of the methods mentioned which physically or chemically permeabilize the cell membrane. Some of these techniques may be successfully adapted for in vivo or ex vivo use, as discussed below.

a. Liposome-Mediated Transfection

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

b. Electroporation

In certain embodiments of the present invention, the expression construct is introduced into the cell via electroporation. Electroporation involves the exposure of a suspension of cells and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

c. Calcium Phosphate Precipitation or DEAE-Dextran Treatment

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using. DEAE-dextran followed by polyethylene glycol. In this manner, reporter plasmids were introduced into mouse myeloma and erythroleukemia cells (Gopal, 1985).

d. Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

e. Direct Microinjection or Sonication Loading

Further embodiments of the present invention include the introduction of the expression construct by direct microinjection or sonication loading. Direct microinjection has been used to introduce nucleic acid constructs into Xenopus oocytes (Harland and Weintraub, 1985), and LTK_ fibroblasts have been transfected with the thymidine kinase gene by sonication loading (Fechheimer et al., 1987).

f. Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

g. Receptor Mediated Transfection

Still further expression constructs that may be employed to deliver the tissue-specific promoter and transforming construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention. Specific delivery in the context of another mammalian cell type is described by Wu and Wu (1993; incorporated herein by reference).

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. In the context of the present invention, the ligand will be chosen to correspond to a receptor specifically expressed on the neuroendocrine target cell population.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

E. Pharmaceutical Compositions

1. Pharmaceutically Acceptable Carriers

Aqueous compositions of the present invention comprise an effective amount of the HBD-3 protein, peptide, epitopic core region, inhibitor, nucleic acid sequence or such like, dissolved or dispersed in a pharmaceutically acceptable carrier or aqueous medium. Aqueous compositions of gene therapy vectors expressing any of the foregoing are also contemplated. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains a HBD-3 agent as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An HBD-3 protein or peptide of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active HBD-3 peptide or agents may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used. Suppositories are solid dosage forms of various weights and shapes, usually medicated, for insertion into the rectum, vagina or the urethra After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

2. Liposomes and Nanocapsules

In certain embodiments, the use of liposomes and/or nanoparticles is contemplated for the introduction of HBD-3 protein, peptides or agents, or gene therapy vectors into host cells. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

F. Therapeutic and Antiseptic Uses

The instant invention comprises a composition and methods for its use in the prevention of microbial growth. It is envisioned th at the peptide may be delivered in a composition by itself or in combination with an one or more additional antimicrobial agents to produce a complementary or synergistic effect. In a further embodiment, the invention also encompasses methods to reduce antimicrobial resistance, caused by any of the seven mechanisms described by Davies (1986) (previously cited), using an antimicrobial peptide and one or more antimicrobial agents or antibiotics. Exemplary bacterial strains that have developed antibiotic resistance by one or more of these mechanisms are set forth in Table 4 (Lorian, 1991).

The antimicrobial peptides have broad spectrum antimicrobial properties effective against both Gram-positive and Gram-negative strains of bacteria and are thus frequently effective to kill strains previously deemed multiply drug resistant. The purified antimicrobial peptide may be used without further modifications or it may be diluted in a pharmaceutically acceptable carrier. Because of the stability of the peptides it is contemplated that the invention may be administered to humans or animals, included in food preparations, pharmaceutical preparations, medicinal and pharmaceutical products, cosmetic products, hygienic products, cleaning products and cleaning agents, as well as any material to which the peptides could be sprayed on or adhered to wherein the inhibition of microbial growth on such a material is desired. In the context of routes of administration, delivery or application, it is envisioned that the antimicrobial peptide will be delivered in a composition that facilitates the maintenance of the antimicrobial properties of the peptides. For example, if the antimicrobial peptide is to be topically administered or placed in hygienic products, cleaning products and cleaning agents, it will be administered in diluent that is properly formulated to retain the proper conformation of the peptide. Due to their immuno-modulatory chemoattractant properties, HBD-3 might be used to augment host defense at mucosal surfaces (Yang, et al. 1999).

The proper dosage of an antimicrobial peptide necessary to prevent microbial growth and proliferation depends upon a number of factors including the types of bacteria that might be present, the environment into which the peptide is being introduced, and the time that the peptide is envisioned to remain in a given area.

It is further contemplated that the antimicrobial peptides of the invention may be used in combination with or to enhance the activity of other antimicrobial agents or antibiotics. Combinations of the peptide with other agents may be useful to allow antibiotics to be used at lower doses due to toxicity concerns, to enhance the activity of antibiotics whose efficacy has been reduced or to effectuate a synergism between the components such that the combination is more effective than the sum of the efficacy of either component independently. Antibiotics which may be combined with an antimicrobial peptide in combination therapy include but are not limited to penicillin, ampicillin, amoxycillin, vancomycin, cycloserine, bacitracin, cephalolsporin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraaminosalicylic acid, and ethambutol. Table 5 (Reese and Betts, 1993), lists the antibiotics generally preferred for use against a given pathogenic bacterium. It is contemplated that the effectiveness of all the antibiotics listed in Table 5 will be increased upon combination with an antimicrobial peptide. Table 6 (Reese and Betts, 1993), itemizes the common pathogenic bacteria that are implicated in focal infections. The present invention is thus contemplated for use against all such infections.

TABLE 4

MECHANISMS OF RESISTANCE TO ANTIMICROBIAL AGENTS

| Antimicrobial Agent | Mechanisms Causing Resistance | EXAMPLES OF ORGANISMS |
|---|---|---|
| Aminoglycosides | Modifying enzymes: acetyltransferases, adenylyl-transferases (nucleotidyl-transferases), phosphotransferases Ribosomal resistance (streptomycin, spectinomycin) | *Enterobacteriaceae, P. aeruginosa, S. aureus, E. faecalis* |
|  | Inadequate drug transport | *E. faecalis, Enterobacteriaceae, M. tuberculosis P. aeruginosa, E. faecalis, P. aeruginosa,* anaerobes |
| β-Lactams | Enzymatic inactivation | *S. aureus, E. faecalis, Enterobacteriaceae, P. aeruginosa, Neisseria* spp., *H. influenzae* |
|  | Low affinity PBPs | *S. pneumoniae, N. gonorrhoeae, S. aureus,* |
|  | Lack of penetration through outer membrane | *P. aeruginosa P. aeruginosa, Enterobacteriaceae* |
| Chloramphenicol | Acetylation | *Enterobacteriaceae, S. aureus,* streptococci, *Bacteroides uniformis* |
|  | Lack of penetration | *P. aeruginosa* |
| Clindamycin, erythromycin, | Ribosomal resistance due to methylation of rRNA | *Streptococci, E. faecalis,* |

TABLE 4-continued

MECHANISMS OF RESISTANCE TO ANTIMICROBIAL AGENTS

| Antimicrobial Agent | Mechanisms Causing Resistance | EXAMPLES OF ORGANISMS |
|---|---|---|
| lincomycin | Inactivation by esterase | *Enterobacteriaceae* |
|  | Decreased penetration | *Enterobacteriaceae S. hominis* |
| Fluoroquinolones | Decreased uptake | *Enterobacteriaceae, P. aeruginosa,* |
|  | Altered target site (DNA gyrase) | staphylococci *Enterobacteriaceae, P. aeruginosa* |
| Lincomycin | Inactivation | *S. aureus* |
| Sulfonamides | Synthesis of an altered or alternative target site (dihydropteroate synthetase) | *Enterobacteriaceae, Neisseria* spp., *P. aeruginosa* |
|  | Lack of penetration | Anaerobes |
|  | Overproduction of PABA | *Neisseria, S. aureus* |
| Tetracycline | Drug efflux | *Enterobacteriaceae,* staphylococci, streptococci |
|  | Protection of ribosome from tetracycline | *Streptococci, E. faecalis, Neisseria* spp., *Mycoplasma* spp. |
|  | Inactivation | Cryptic gene found in *B. fragilis,* expressed resistance in *E. coli* |
| Trimethoprim | Synthesis of an altered or alternative target site (dihydrofolate reductase) | *Enterobacteriaceae, V. cholerae,* staphylococci |
|  | Lack of penetration |  |
|  | Ability to use alternative pathway | *P. aeruginosa* |
|  | Overproduction of dihydrofolate reductase | Enterococci *H. influenzae* |
| Vancomycin | ? | Pediococci, Leuconostoc |
|  | ?Blocking of target site | spp. (intrinsic) Enterococci (acquired) |

TABLE 5

ANTIBIOTICS OF CHOICE FOR COMMON PATHOGENS

| Pathogen | Antibiotic of First Choice[a] | Alternative Agents[a] |
|---|---|---|
| Gram-positive *cocci* |  |  |
| *Staphylococcus aureus* or *S. epidermidis* Non-penicillinase-producing | Penicillin | A first-generation cephalosporin, vancomycin, imipenem, or clindamycin; a fluoroquinolone[b] |
| Penicillinase-producing | Penicillinase-resistant penicillin (e.g., oxacillin or nafcillin) | A first-generation cephalosporin, vancomycin, clindamycin, imipenem, amoxicillin-clavulanic acid, ticarcillin-clavulanic acid, ampicillin-sulbactam; a fluoroquinolone[b] |
|  | Vancomycin with or without | TMP-SMZ, minocycline |

TABLE 5-continued

ANTIBIOTICS OF CHOICE FOR COMMON PATHOGENS

| Pathogen | Antibiotic of First Choice[a] | Alternative Agents[a] |
|---|---|---|
| Methicillin-resistant *Streptococci* | gentamicin and/or rifampin | |
| Group A, C, G | Penicillin | A cephalosporin[a], vancomycin, erythromycin; clarithromycin; azithromycin; clindamycin |
| Group B | Penicillin (or ampicillin) | A cephalosporin[a], vancomycin, or erythromycin |
| *Enterococcus* Endocarditis or other serious infection | Penicillin (or ampicillin) with gentamicin | Vancomycin with gentamicin |
| Uncomplicated urinary tract infection | Ampicillin or amoxicillin | A fluoroquinolone, nitrofurantoin |
| *Viridans* group | Penicillin G (with or without gentamicin) | A cephalosporin[a], vancomycin |
| *S. bovis* | Penicillin G | A cephalosporin[a], vancomycin |
| *S. pneumoniae* | Penicillin G | A cephalosporin[a], erythromycin, chloramphenicol, vancomycin |
| Gram-negative *cocci* | | |
| *Neisseria gonorrhoeae* | Ceftriaxone | Spectinomycin, a fluoroquinolone, cefoxitin, cefixime, cefotaxime (see Appendix E) |
| *N. meningitidis* | Penicillin G | Third-generation cephalosporin, chloramphenicol |
| *Moraxella* (*Branhamella*) *catarrhalis* | TMP-SMZ | Amoxicillin-clavulanic acid; an erythromycin; clarithromycin azithromycin, cefuroxime, cefixime, third-generation cephalosporin, tetracycline |
| Gram-positive *bacilli* | | |
| *Clostridium perfringens* (and *Clostridium* sp.) | Penicillin G | Chloramphenicol, metronidazole, or clindamycin |
| *Listeria monocytogenes* | Ampicillin with or without gentamicin | TMP-SMZ |
| Gram-negative *bacilli* | | |
| *Acinetobacter* | Imipenem | Tobramycin, gentamicin, or amikacin, usually with ticarcillin or piperacillin (or similar agent); TMP-SMZ |
| *Aeromonas hydrophila* | TMP-SMZ | Gentamicin, tobramycin; imipenem; a fluoroquinolone |
| *Bacteroides* *Bacteroides* sp. (*oropharyngeal*) | Penicillin G | Clindamycin, cefoxitin, metronidazole, chloramphenicol, cefotetan, ampicillin-sulbactam |
| *B. fragilis* strains (gastrointestinal strains) | Metronidazole | Clindamycin; ampicillin-sulbactam; imipenem; cefoxitin[c]; cefotetan[c]; ticarcillin-clavulanic acid; piperacillin[c]; chloramphenicol; cefmetazole[c] |
| *Campylobacter fetus, jejuni* | A fluoroquinolone (adults) or an erythromycin | A tetracycline, gentamicin |
| *Enterobacter* sp. | Imipenem | An aminoglycoside and piperacillin or ticarcilin or mezlocillin; a third-generation cephalosporin[d]; TMP-SMZ; aztreonam; a fluoroquinolone |
| *Escherichia coli* Uncomplicated urinary tract infection | TMP-SMZ A cephalosporin[e] | A cephalosporin or a fluoroquinolone Ampicillin with or without an |

TABLE 5-continued

ANTIBIOTICS OF CHOICE FOR COMMON PATHOGENS

| Pathogen | Antibiotic of First Choice[a] | Alternative Agents[a] |
|---|---|---|
| Recurrent or systemic infection | | aminoglycoside, TMP-SMZ, oral fluoroquinolones useful in recurrent infections, ampicillin-sulbactam, ticarcillin-clavulanic acid, aztreonam |
| *Haemophilus influenzae* | | |
| (*coccobacillary*) | Cefotaxime or ceftriaxone | Chloramphenicol; cefuroxime for pneumonia) |
| Life-threatening infections | TMP-SMZ | Ampicillin or amoxicillin; cefuroxime; a sulfonamide with |
| Upper respiratory infections and bronchitis | | or without an erythromycin; cefuroxime-axetil; third-generation cephalosporin, amoxicillin-clavulanic acid, cefaclor, tetracycline; clarithromycin; azithromycin |
| *Klebsiella pneumoniae* | A cephalosporin[e] | An aminoglycoside, imipenem, TMP-SMZ, ticarcillin-clavulanic acid, ampicillin-sulbactam, aztreonam, a fluoroquinolone; amoxicillin-clavulanic acid |
| *Legionella* spp. | Erythromycin with rifampin | TMP-SMZ; clarithromycin; azithromycin; ciprofloxacin |
| *Pasteurella multocida* | Penicillin G | Tetracycline, cefuroxime, amoxicillin-clavulanic acid, ampicillin-sulbactam |
| *Proteus* sp. | Cefotaxime, ceftizoxime, or ceftriaxone[f] | An aminoglycoside; ticarcillin or piperacillin or mezlocillin; TMP-SMZ; amoxicillin-clavulanic acid; ticarcillin-clavulanic acid, ampicillin-sulbactam; a fluoroquinolone; aztreonam; imipenem |
| *Providencia stuartii* | Cefotaxime, ceftizoxime, or ceftriaxone[f] | Imipenem; an aminoglycoside often combined with ticarcillin or piperacillin or similar agent; ticarcillin-clavulanic acid; TMP-SMZ, a fluoroquinolone; aztreonam |
| *Pseudomonas aeruginosa* (nonurinary tract infection) | Gentamicin or tobramycin or amikacin (combined with ticarcillin, piperacillin, etc. for serious infections) Ciprofloxacin | An aminoglycoside and ceftazidime; imipenem, or aztreonam plus an aminoglycoside; ciprofloxacin |
| (urinary tract infections) | | Carbenicillin; ticarcillin, piperacillin, or mezlocillin; ceftazidime; imipenem; aztreonam; an aminoglycoside |
| *Pseudomonas cepacia* | TMP-SMZ | Ceftazidime, chloramphenicol |
| *Salmonella typhi* | Ceftriaxone | Ampicillin, amoxicillin, TMP-SMZ, |
| Other species | Cefotaxime or ceftriaxone | chloramphenicol; a fluoroquinolone Ampicillin or amoxicillin, TMP-SMZ, chloramphenicol; a fluoroquinolone |
| *Serratia* | Cefotaxime, ceftizoxime, or ceftriaxone[f] | Gentamicin or amikacin; imipenem; TMP-SMZ; ticarcillin, piperacillin, or meziocillin; aztreonam; a fluoroquinolone |
| *Shigella* | A fluoroquinolone | TMP-SMZ; ceftriaxone; ampicillin |
| *Vibrio cholerae* (*chlorea*) | A tetracycline | TMP-SMZ; a fluoroquinolone |

TABLE 5-continued

ANTIBIOTICS OF CHOICE FOR COMMON PATHOGENS

| Pathogen | Antibiotic of First Choice[a] | Alternative Agents[a] |
|---|---|---|
| *Vibrio vulnificus* | A tetracycline | Cefotaxime |
| *Xanthomonas (Pseudomonas) maltophilia* | TMP-SMZ | Minocycline, ceftazidime, a fluoroquinolone |
| *Yersinia enterocolitica* | TMP-SMZ | A fluoroquinolone; an aminoglycoside; cefotaxime or ceftizoxime |
| *Yersinia pestis* (plague) | Streptomycin | A tetracycline; chloramphenicol; gentamicin |

Key: TMP-SMZ = trimethoprim-sulfamethoxazole.
[a]Choice presumes susceptibility studies indicate that the pathogen is susceptible to the agent.
[b]The experience with fluoroquinolone use in staphylococcal infections is relatively limited. The fluoroquinolones should be used only in adults.
[c]Up to 15–20% of strains may be resistant.
[d]*Enterobacter* spp. may develop resistance to the cephalosporins.
[e]Specific choice will depend on susceptibility studies. Third-generation cephalosporins may be exquisitely active against many Gram-negative bacilli (e.g., *E. coli*, Klebsiella sp.). In some geographic areas, 20–25% of community-acquired *E. coli* infections may be resistant to ampicillin (amoxicillin).
[f]In severely ill patients, this is often combined with an aminoglycoside while awaiting susceptibility data.

TABLE 6

COMMON PATHOGENS IN FOCAL INFECTIONS

| Presumed location of Infection | Common pathogens | Gram stain Characteristics of exudate-if available |
|---|---|---|
| Urinary tract infections | Community-acquired: *Escherichia coli* | GNB |
|  | | GNB |
|  | Recurrent or nosocomial: *E. coli*: |  |
|  | *Klebsiella, Proteus, Pseudomonas* sp. *Enterococci* | GPC |
| Intravenous catheter phlebitis and/or sepsis |  |  |
| Peripheral catheter | *Staphylococcus aureus* or *S. epidermidis* | GPC |
|  | *Klebsiella, Enterobacter, Pseudomonas* sp. | GNB |
| Hyperalimentation line | *Candida* sp., *S. aureus*, *S. epidermidis*, enterococci | Budding yeast; GPC |
|  | *Klebsiella, Enterobacter* sp., etc. | GNB |
| Arteriovenous shunt | *S. aureus, S. epidermidis* | GPC |
| Septic bursitis | *S. aureus* | GPC |
| Biliary tract | *E. coli, Klebsiella* sp., and enterococci; *Bacteroides fragilis* (in elderly patients), Clostridia sp. |  |
| Intra-abdominal abscess, peritonitis, or large bowel perforation; diverticulitis[a] | *E. coli* | GNB |
|  | *B. fragilis* | GNB (thin, irregularly stained) |
|  | *Klebsiella* sp. | GNB |
|  | (*Enterococci*) | GPC |
| Burn wounds | Early: *S. aureus*, streptococci |  |
|  | Later: Gram-negative bacilli, fungi |  |
| Cellulitis, wound and soft tissue infections | *S. aureus* | GPC |
|  | *Streptococci* | GPC |
|  | *Clostridium* sp. | GPB |
| Meningitis | See Appendix C |  |
| Pneumonia | See Appendix D |  |
| Pelvic abscess, postabortal or postpartal | Anaerobic streptococci | GPC |
|  | *B. fragilis* | GNB (thin, irregularly stained) |

TABLE 6-continued

COMMON PATHOGENS IN FOCAL INFECTIONS

| Presumed location of Infection | Common pathogens | Gram stain Characteristics of exudate-if available |
|---|---|---|
| | *Clostridium* sp. | GPB |
| | *E. coli* | GNB |
| | Enterococci | GPC |
| Septic arthritis | *S. aureus* | GPC |
| | *Haemophilus influenzae* (in children younger than 6 yr) | GNC |
| | | GPC |
| | Group B *streptococci* (in neonates) | GNB |
| | Gram-negative organisms[b] | |
| Acute osteomyelitis | *S. aureus* | GPC |
| | *H. influenzae* (in children younger than 6 yr) | GNC |
| | Group B *streptococci* (in neonates) | GPC |
| | Gram-negative organisms[b] | GNB |

Key: GNB = Gram-negative *bacilli*; GPC = Gram-positive *cocci*; GPB = Gram-positive *bacilli*; GNC = Gram-negative *coccobacilli*.
[a]The precise role of *enterococci* in intra-abdominal infections is unclear. In mild to moderate infections, it may not be necessary to provide antibiotic activity against *enterococci*.
[b]In high-risk patients (e.g., immunocompromised, elderly, IV drug abusers, diabetics, debilitated patients).

To reduce the resistance of a microorganism to an antimicrobial agent, as exemplified by reducing the resistance of a bacterium to an antibiotic, or to kill a microorganism or bacterium, one would generally contact the microorganism or bacterium with an effective amount of the antibiotic or antimicrobial agent in combination with an amount of an antimicrobial peptide effective to inhibit growth of the microorganism or bacterium. In terms of killing or reducing the resistance of a bacterium, one would contact the bacterium with an effective amount of an antibiotic in combination with an amount of an antimicrobial peptide effective to inhibit growth and/or proliferation in the bacterium.

The terms "microbe," "microorganism" and "bacterium" are used for simplicity and it will be understood that the invention is suitable for use against a population of microorganisms, ie., "bacteria".

In the context of bacterial or microbial infections, a person of ordinary skill would recognize the wide variety of potential pathogens. As an exemplary list, bacterial infections, are deemed to include, but not be limited to, the 83 or more distinct serotypes of *pneumococci, streptococci* such as *S. pyrogenes, S. agalactiae, S. equi, S. canis, S. bovis, S. equinus, S. anginosus, S. sanguis, S. salivarius, S. mitis, S. mutans*, other viridans *streptococci, peptostreptococci*, other related species of *streptococci, enterococci* such as *Enterococcus faecalis, Enterococcus faecium, Staphylococci*, such as *Staphylococcus epidermidis, Staphylococcus aureus*, particularly in the nasopharynx, *Hemophilus influenzae*, pseudomonas species such as *Pseudomonas aeruginosa, Pseudomonas pseudomallei, Pseudomonas mallei*, brucellas such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocardia asteroides, Bacteroides* species, *Actinomycetes* species, *Treponema pallidum, Leptospirosa* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enterobacter* species, *Bacteriodes and Legionella* species and the like. In addition, the invention may prove useful in controlling protozoan or macroscopic infections by organisms such as *Cryptosporidium, Isospora belli, Toxoplasma gondii, Trichomonas vaginalis, Cyclospora* species, for example, and for *Chlamydia trachomatis* and other *Chlamydia* infections such as *Chlamydia psittaci*, or *Chlamydia pneumoniae*, for example.

The microorganism, e.g., bacterium, or population thereof, may be contacted either in vitro or in vivo. Contacting in vivo may be achieved by administering to an animal (including a human patient) that has, or is suspected to have a microbial or bacterial infection, a therapeutically effective amount of pharmacologically acceptable antimicrobial peptide formulation in alone or in combination with a therapeutic amount of a pharmacologically acceptable formulation of a antibiotic agent. The invention may thus be employed to treat both systemic and localized microbial and bacterial infections by introducing the combination of agents into the general circulation or by applying the combination, e.g., topically to a specific site, such as a wound or burn, or to the eye, ear or other site of infection.

Where an antimicrobial peptide is used in combination with other antimicrobial agents or antibiotics, an "effective amount of an antimicrobial agent or antibiotic" means an amount, or dose, within the range normally given or prescribed. Such ranges are well established in routine clinical practice and will thus be known to those of skill in the art. Appropriate oral and parenteral doses and treatment regimens are further detailed herein in Table 7 and Table 8. As this invention provides for enhanced microbial and/or bacterial killing, it will be appreciated that effective amounts of an antimicrobial agent or antibiotic may be used that are lower than the standard doses previously recommended when the antimicrobial or antibiotic is combined with a antimicrobial peptide.

Naturally, in confirming the optimal therapeutic dose for antimicrobial peptides, first animal studies and then clinical trials would be conducted, as is routinely practiced in the art. Animal studies are common in the art and are further described herein (Example 2) and in publications such as Lorian (1991, pp. 746–786, incorporated herein by reference) and Cleeland and Squires (incorporated herein by reference, from within the Lorian text).

The $ID_{50}/IC_{50}$ ratio required for safe use of the proposed inhibitor-antimicrobial peptide or combinations of peptide with other antimicrobial agents will be assessed by determining the $ID_{50}$ (median lethal toxic dosage) and the $IC_{50}$ (median effective therapeutic dosage) in experimental animals. The optimal dose for human subjects is then defined by fine-tuning the range in clinical trials. In the case of $DI_{50}$, the inhibitor is usually administered to mice or rats (orally or intraperitoneal) at several doses (usually 4–5) in the lethal rage. The dose in mg/kg is plotted against % mortality and the dose at 50% represents the $ID_{50}$ (Klaassen, 1990). The $IC_{50}$ is determined in a similar fashion as described by Cleeland and Squires (1991).

In a clinical trial, the therapeutic dose would be determined by maximizing the benefit to the patient, whilst minimizing any side-effects or associated toxicities. Throughout the detailed examples, various therapeutic ranges are listed. Unless otherwise stated, these ranges refer to the amount of an agent to be administered orally.

In optimizing a therapeutic dose within the ranges disclosed herein, one would not use the upper limit of the range as the starting point in a clinical trial due to patient heterogeneity. Starting with a lower or mid-range dose level, and then increasing the dose will limit the possibility of eliciting a toxic or untoward reaction in any given patient or subset of patients. The presence of some side-effects or certain toxic reactions per se would not, of course, limit the utility of the invention, as it is well known that most beneficial drugs also produce a limited amount of undesirable effects in certain patients. Also, a variety of means are available to the skilled practitioner to counteract certain side-effects, such as using vitamin $B_{12}$ in association with $N_2O$ treatment (Ostreicher, 1994).

Zak and Sande (1981) reported on the correlation between the in vitro and in vivo activity of a 1000 compounds that were randomly screened for antimicrobial activity. The important finding in this study is that negative in vitro data is particularly accurate, with the negative in vitro results showing more than a 99% correlation with negative in vivo activity. This is meaningful in the context of the present invention as one or more in vitro assays will be conducted prior to using any given combination in a clinical setting. Any negative result obtained in such an assay will thus be of value, allowing efforts to be more usefully directed.

In the treatment of animals or human patients with combination therapy, there are various appropriate formulations and treatment regimens that may be used. For example, the antimicrobial peptide and second agent(s) may be administered to an animal simultaneously, e.g., in the form of a single composition that includes the antimicrobial peptide and second agent, or by using at least two distinct compositions. The antimicrobial agent could also be administered to the animal prior to the second agent or the second agent may be given prior to the antimicrobial peptide.

Multiple combinations may also be used, such as more than one antimicrobial peptide used with one second agent or more than one second agent. Different classes second agents and antimicrobial peptides may be combined, naturally following the general guidelines known in the art regarding drug interactions. Typically, between one and about five distinct antimicrobial agents are contemplated for use along with between one and about six antimicrobial peptides.

Further embodiments of the invention include therapeutic kits that comprise, in suitable container means, a pharmaceutical formulation of at least one antimicrobial peptide and a pharmaceutical formulation of at least one antimicrobial agent or antibiotic. The antimicrobial peptide and antimicrobial agent or antibiotic may be contained within a single container means, or a plurality of distinct containers may be employed.

Depending on the circumstances, antimicrobial agents may be employed in oral or parenteral treatment regimens. Appropriate doses are well known to those of skill in the art and are described in various publications, such as (Reese and Betts, 1993; incorporated herein by reference). Table 7 and Table 8 (taken from Reese and Betts, 1993) are included herein to provide ready reference to the currently recommended doses of a variety of antimicrobial agents.

Following are definitions of terms that are used in Table 7 and Table 8: qid (4 times daily), tid (3 times daily), bid (twice daily), qd (once daily), q4h (every 4 hours around the clock), q6h (every 6 hours around the clock) and q8h (every 8 hours around the clock).

TABLE 7

COMMON ANTIBIOTICS AND USUAL ORAL DOSES

| ANTIBIOTIC | DOSAGE |
|---|---|
| Penicillin V | 250 mg qid |
| Rugby (generic) | |
| V-cillin K | |
| Dicloxacillin | 250 mg qid |
| Glenlawn (generic) | |
| Dynapen | |
| Cloxacillin (Tegopen) | 250 mg qid |
| Amoxicillin | 250 mg tid |
| Rugby (generic) | |
| Polymox | |
| Ampicillin | 250 mg qid |
| Moore (generic) | |
| Polycillin | |
| Augmentin | tid |
| 250-mg tablets | |
| chewables (250 mg) | |
| 125-mg (suspension) | |
| chewables (125 mg) | |
| | 382 mg qid (1 tb) |
| Carbenicillin (Geocillin) | 2 tab qid |
| Cephalexin | 250 mg qid |
| Rugby (generic) | |
| Keflex | |
| Rugby (generic) | 500 mg qid |
| Keflex | |
| Cefadroxil | 1 gm bid |
| Rugby (generic) | |
| Duricef | |
| Cephradine | 250 mg qid |
| Rugby (generic | |
| Velosef | |
| Rugby (generic) | 500 mg qid |
| Velosef | |
| Cefaclor | 250 mg tid |
| Ceclor | |
| Cefuroxime axetil | |
| Ceftin | 125 mg bid |
| | 250 mg bid |
| | 500 mg bid |

TABLE 7-continued

COMMON ANTIBIOTICS AND USUAL ORAL DOSES

| ANTIBIOTIC | DOSAGE |
|---|---|
| Cefixime | 400 mg q24h |
| Suprax | |
| Cefprozil | |
| Cefzil | 250 mg q12h |
| Loracarbef (Lorabid) | 200 mg bid |
| Cefpodoxime proxetil | 200 mg bid |
| (Vantin) | |
| Clindamycin | 300 mg q8h |
| Cleocin | |
| TMP/SMZ | 1 double-strength bid |
| Bactrim | |
| Septra | |
| (generic) | |
| Trimethoprim | 100 mg bid |
| Rugby (generic) | |
| Proloprim | |
| Erythromycin (base) | 250 mg qid |
| Abbott | |
| E-mycin (delayed release) | |
| Erythromycin stearate | 250 mg qid |
| Rugby (generic) | |
| Azithromycin | 1 g once only 500 mg, |
| Zithromax | day 1, plus 250 mg, day 2–5 |
| Clarithromycin | 250 mg bid |
| Biaxin | 500 mg bid |
| Tetracycline hydrochloride | 250 mg qid |
| Mylan | |
| Sumycin 250 | |
| Doxycycline | 100 mg qd (with 200– mg initial load) |
| Lederle (generic) | |
| Vibramycin | |
| Vancomycin | |
| Vancocin HCl (oral soln/powder) | Capsules 125 mg q6h PO |
| Metronidazole | 250 mg qid |
| Rugby (generic) | |
| Flagyl | |
| Norfloxacin | 400 mg bid |
| Noroxin | |
| Ciprofloxacin | 250 mg bid |
| Cipro | 500 mg bid |
| | 750 mg bid |
| Ofloxacin | |
| Floxin | 200 mg bid |
| | 300 mg bid |
| | 400 mg bid |
| Lomefloxacin Maxaquin | 400 mg once qd |

TABLE 8

COMMON ANTIBIOTICS AND USUAL PARENTERAL DOSES

| ANTIBIOTIC | DOSAGE |
|---|---|
| Penicillin G | 2,400,000 units |
| Pfizerpen G (Pfizer) | 12 million units |
| Oxacillin | 12 g |
| Prostaphlin (Bristol) | |
| Nafcillin | 12 g |
| Nafcil (Bristol) | |
| Ampicillin | 6 g |
| Omnipen (Wyeth) | |
| Ticarcillin | 18 g |
| Ticar (Beecham) | |
| Piperacillin | 18 g |
| Pipracil (Lederle) | 16 g |
| Mezlocillin | 18 g |
| Mezlin (Miles) | 16 g |
| Ticarcillin-clavulanate | 18 g/0.6 g |
| Timentin (Beecham) | 12 g/0.4 g |
| Ampicillin-sulbactam | 6 g |
| Unasyn (Roerig) | 12 g |
| Cephalothin | 9 g (1.5 g q4h) |
| Keflin (Lilly) | |
| Cefazolin | 4 g (1 g q6h) |
| Ancef(SKF) | 3 g (1 g q8h) |
| Cefuroxime | 6 g 2.25 g (750 mg q8h) |
| Zinacef(Glaxo) | 4.5 g (1.5 g q8h) |
| Cefamandole | 9 g (1.5 g q4h) |
| Mandol (Lilly) | |
| Cefoxitin | 8 g (2 g q6h) |
| Mefoxin (MSD) | 6 g (2 g q8h) |
| Cefonicid | 1 g q12h |
| Monicid (SKF) | |
| Cefotetan | 2 g q12h |
| Cefotan (Stuart) | |
| Cefmetazole | 2 g q8h |
| Zefazone (Upjohn) | |
| Ceftriaxone | 2 g (2.0 g q24h) |
| Rocephin (Roche) | 1 g (1.0 g q24h) |
| Ceftazidime | 6 g (2 g q8h) |
| Fortax (Glaxo) | |
| Taxicef (SKF) | |
| Tozidime (Lilly) | |
| Cefotaxime | 2 g q6h |
| Claforan (Hoechst) | 2 g q8h |
| Cefoperazone | 8 g (2 g q6h) |
| Cefobid (Pfizer) | 6 g (2 g q8h) |
| Ceftizoxime | (2 g q8h) |
| Ceftizox (SKF) | |
| Aztreonam | 2 g q8h |
| Azactam (Squibb) | 1 g q8h |
| Imipenem | 2000 mg (500 mg 16h) |
| Primaxin (MSD) | |
| Gentamicin | |
| Garamycin (Schering) | 360 mg (1.5 mg/kg q8h for an 80-kg patient) |
| (generic) (Elkins-Sinn) | |
| Tobramycin | 360 mg (1.5 mg/kg q8h |
| Nebcin (Dista) | for an 80-kg patient) |
| Amikacin | 1200 mg (7.5 mg/kg |
| Amikin (Bristol) | q12h for an 80-kg patient) |
| Clindamycin | 2400 mg (600 mg q6h) |
| Cleocin (Upjohn) | 2700 mg (900 mg q8h) |
| | 1800 mg (600 mg q8h) |
| Chloramphenicol | 4 g (1 g q6h) |
| Chloromycetin (P/D) | |
| TMP/SMZ | 1400 mg TMP (5 mg |
| Septra (Burroughs Wellcom) | TMP/kg q6h for a 70-kg patient) |
| | 700 mg TMP (5 mg TMP/kg q12h for a 70-kg patient) |
| Erythromycin | 2000 mg (500 mg q6h) |
| Erythromycin (Elkins-Sinn) | |
| Doxycycline | 200 mg (100 mg q12h) |
| Vibramycin (Pfizer) | |
| Vancomycin | 2000 mg (500 mg q6h) |
| Vancocin (Lilly) | |
| Metronidazole | 2000 mg (500 mg q6h) |
| (generic) (Elkins-Sinn) | |
| Ciprofloxacin | 200 mg q12h |
| Cipro | 400 mg q12h |
| Pentamidine | 280 mg (4 mg/kg q24h |
| Pentam (LyphoMed) | for a 70-kg patient) |

The effectiveness of erythromycin and lincomycin against a wide variety of organisms is shown in Table 9 (taken from Lorian, 1991) to illustrate the range of antibiotic resistance acquired by various bacterial strains. The data presented in the tables of the present specification is merely illustrative and is considered another tool to enable the straightforward comparison of raw data with accepted clinical practice and to allow the determination of appropriate doses of combined agents for clinical use.

TABLE 9

SUSCEPTIBILITY TO ANTIBIOTICS

| Species | (n) | Range | MIC$_{50}$ | MIC$_{90}$ |
|---|---|---|---|---|
| ERYTHROMYCIN | | | | |
| Bacillus spp. | 20 | 0.03–2 | 0.25 | 2 |
| Bacteroides fragilis | 97 | 0.25–16 | 1 | 8 |
| Bordetella bronchiseptica | 11 | 4–32 | 8 | 32 |
| Bordetella parapertussis | 46 | 0.125–4 | 0.25 | 0.25 |
| Bordetella pertussis | 32 | 1–0.5 | 0.25 | 0.25 |
| Bordetella pertussis | 75 | 0.125–0.5 | 0.125 | 0.125 |
| Borrelia burgdorferi | 10 | 0.03–0.125 | 0.03 | 0.06 |
| Branhamella (Moraxella) catarrhalis | 20 | 0.125–0.5 | 0.25 | 0.25 |
| Branhamella (Moraxella) catarrhalis | 20 | 0.125–0.5 | 0.25 | 1 |
| Branhamella (Moraxella) catarrhalis (non β-lactamase producer) | 40 | 0.06–0.5 | 0.25 | 0.5 |
| Branhamella (Moraxella) catarrhalis (non β-lactamase producer) | 13 | 0.03–0.125 | 0.06 | 0.06 |
| Branhamella (Moraxella) catarrhalis (non β-lactamase producer) | 14 | 0.06–1 | 0.125 | 1 |
| Branhamella (Moraxella) catarrhalis (non β-lactamase producer) | 16 | 0.015–1 | 0.06 | 0.25 |
| Branhamella (Moraxella) catarrhalis (β-lactamase producer) | 47 | 0.06–1 | 0.25 | 0.5 |
| Branhamella (Moraxella) catarrhalis (β-lactamase producer) | 58 | 0.03–0.25 | 0.125 | 0.125 |
| Branhamella (Moraxella) catarrhalis (β-lactamase producer) | 160 | 0.06–8 | 0.25 | 0.5 |
| Branhamella (Moraxella) catarrhalis (β-lactamase producer) | 35 | 0.03–0.125 | 0.06 | 0.06 |
| Campylobacter jejuni | 25 | 0.5–8 | 1 | 4 |
| Campylobacter jejuni | 16 | 0.125–4 | 0.25 | 2 |
| Campylobacter pylori | 56 | 0.25–16 | 0.5 | 1 |
| Campylobacter pylori | 13 | 0.125–0.25 | 0.125 | 0.25 |
| Corynebacterium JK | 102 | 0.5–128 | 128 | 128 |
| Corynebacterium JK | 19 | 0.125–64 | 2 | 64 |
| Enterococcus faecalis | 26 | 1–64 | 1 | 4 |
| Enterococcus faecalis | 50 | 0.06–64 | 4 | 64 |
| Enterococcus faecalis | 86 | 0.125–64 | 1 | 64 |
| Enterococcus faecalis | 97 | 0.125–128 | 2 | 128 |
| Enterococcus faecium | 14 | 0.06–64 | 1 | 64 |
| Enterococcus spp. | 35 | 0.06–32 | 2 | 32 |
| Haemophilus ducreyi | 122 | ?–0.125 | 0.004 | 0.06 |
| Haemophilus influenzae | 145 | 0.5–8 | 2 | 2 |
| Haemophilus influenzae | 97 | 0.25–16 | 1 | 4 |
| Haemophilus influenzae (non β-lactamase producer) | 22 | 0.125–8 | 2 | 4 |
| Haemophilus influenzae (non β-lactamase producer) | 137 | 0.06–8 | 4 | 8 |
| Haemophilus influenzae (β-lactamase producer) | 46 | 0.06–8 | 4 | 8 |
| Haemophilus influenzae (β-lactamase producer) | 17 | 0.25–4 | 2 | 4 |
| Haemophilus influenzae (penicillin susceptible) | 22 | 0.25–16 | 8 | 16 |
| Haemophilus influenzae (penicillin resistant) | 20 | 8–16 | 8 | 16 |
| Haemophilus parainfluenzae | 13 | 0.5–8 | 2 | 4 |
| Legionella spp. | 23 | 0.03–0.25 | 0.125 | 0.25 |
| Legionella pneumophila | 31 | 0.0075–0.25 | 0.06 | 0.125 |
| Legionella pneumophila | 48 | 0.03–2 | 0.25 | 0.5 |
| Legionella pneumophila | 25 | 0.125–1 | 0.25 | 1 |
| Listeria monocytogenes | 13 | 0.5–1 | 0.5 | 0.5 |
| Listeria monocytogenes | 16 | 0.125–2 | 0.25 | 1 |
| Listeria monocytogenes | 65 | 0.06–32 | 0.125 | 32 |
| Mycoplasma hominis | 26 | 128 | 128 | 128 |
| Mycoplasma hominis | 20 | 256 | 256 | 256 |
| Mycoplasma pneumoniae | 10 | 0.06–8 | 0.06 | 0.06 |
| Mycoplasma pneumoniae | 14 | 0.004–0.03 | 0.004 | 0.004 |
| Neisseria gonorrhoeae | 19 | 0.0075–8 | 0.25 | 1 |
| Neisseria gonorrhoeae (non β-lactamase producer) | 73 | 0.015–4 | 0.25 | 2 |
| Neisseria gonorrhoeae (non β-lactamase producer) | 78 | 0.03–2 | 0.25 | 1 |
| Neisseria gonorrhoeae (β-lactamase producer) | 12 | 0.03–4 | 0.5 | 2 |
| Neisseria gonorrhoeae (β-lactamase producer) | 17 | 1–4 | 2 | 4 |
| Neisseria meningitidis | 19 | 0.5–8 | 1 | 8 |
| Nocardia asteroides | 78 | 0.25–8 | 8 | 8 |
| Staphylococcus aureus | 44 | 0.125–1 | 0.125 | 0.5 |
| Staphylococcus aureus | 100 | 0.25–128 | 0.5 | 4 |
| Staphylococcus aureus (penicillin susceptible) | 20 | 0.125–0.5 | 0.5 | 0.5 |
| Staphylococcus aureus (penicillin susceptible) | 35 | 0.06–32 | 0.25 | 0.5 |
| Staphylococcus aureus (penicillin resistant) | 35 | 0.25–32 | 0.25 | 32 |
| Staphylococcus aureus (methicillin susceptible) | 28 | 0.125–1 | 0.25 | 0.5 |
| Staphylococcus aureus (methicillin susceptible) | 97 | 0.125–64 | 0.25 | 64 |
| Staphylococcus aureus (methicillin susceptible) | 20 | 0.125–1 | 0.5 | 0.5 |
| Staphylococcus aureus (methicillin resistant) | 17 | 0.5–128 | 128 | 128 |
| Staphylococcus aureus (methicillin resistant) | 15 | 64 | 64 | 64 |
| Staphylococcus aureus (methicillin resistant) | 20 | 64 | 64 | 64 |
| Staphylococcus aureus (methicillin resistant) | 30 | 0.06–32 | 32 | 32 |
| Staphylococcus coagulase f | 10 | 0.125–4 | 0.25 | 2 |
| Staphylococcus coagulase f | 100 | 0.125–64 | 0.25 | 64 |
| Staphylococcus coagulase f (non β-lactamase producer) | 12 | 0.03–8 | 0.125 | 0.25 |
| Staphylococcus coagulase f (β-lactamase producer) | 38 | 0.06–16 | 0.125 | 4 |
| Staphylococcus epidermidis | 50 | 0.125–64 | 64 | 64 |
| Staphylococcus haemolyticus | 20 | 0.125–64 | 64 | 64 |
| Staphylococcus hominis | 20 | 0.125–64 | 64 | 64 |
| Streptococcus agalactiae | 20 | 0.03–0.25 | 0.03 | 0.125 |
| Streptococcus agalactiae | 34 | 0.015–0.06 | 0.03 | 0.03 |
| Streptococcus pneumoniae | 58 | 0.03–0.25 | 0.06 | 0.125 |
| Streptococcus pneumoniae | 91 | 0.125–4 | 0.125 | 0.125 |
| Streptococcus pneumoniae | 50 | 0.015–0.06 | 0.03 | 0.03 |
| Streptococcus pneumoniae | 16 | 0.03–0.125 | 0.06 | 0.125 |
| Streptococcus pneumoniae | 26 | 0.015–0.25 | 0.03 | 0.06 |
| Streptococcus pneumoniae | 50 | 0.03–0.125 | 0.06 | 0.06 |
| Streptococcus pyogenes | 19 | 0.03–0.25 | 0.06 | 0.125 |
| Streptococcus pyogenes | 20 | 0.03–0.25 | 0.06 | 0.125 |
| Streptococcus pyogenes | 33 | 0.015–0.03 | 0.03 | 0.03 |
| Streptococcus pyogenes | 20 | 0.06–32 | 0.125 | 32 |
| Streptococcus spp. | 22 | 0.015–0.25 | 0.03 | 0.06 |
| Streptococcus spp. | 107 | 0.004–2 | 0.03 | 1 |
| Ureaplasma urealyticum | 28 | 0.015–256 | 2 | 256 |
| Ureaplasma urealyticum | 19 | 8–128 | 16 | 32 |
| LINCOMYCIN | | | | |
| Mycoplasma hominis | 28 | 0.5–16 | 2 | 4 |
| Mycoplasma pneumoniae | 11 | 2–32 | 8 | 32 |
| Staphylococcus aureus | 100 | 0.5–512 | 1 | 1 |
| Ureaplasma urealyticum | 19 | 64–128 | 128 | 128 |

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Genomics-based Approach for the Identification of Novel Human β-defensins

A human BAC library (CITB-978SK-B and CITB-HSP-C, Cat. # 96011, Research Genetics, Huntsville, Ala.) was screened by PCR using primers designed to the human β-defensin-2 cDNA (Liu et al., 1998). BACs that were positive by PCR for the HBD-2 gene were then sequenced (Genome Sequencing Centre, Institute of Molecular Biotechnology, Jena, Germany). To generate a continuous DNA sequence, the sequences from the BAC clones containing HBD-2 were aligned using the Sequencher program (Gene Codes Corporation, Ann Arbor, Mich.). The sequence from each BAC clone was analyzed for novel β-defensin genes utilizing the BLASTp program from the NCBI website. First, genomic BAC sequence was translated in all six possible reading frames using the ExPASy website and then compared to the protein sequences encoded by the HNP-1 and HBD-2 genes as representatives of the α- and β-defensins. The identification of novel defensins was based on the presence of the conserved six cysteine motifs characteristic of the α-(C-X-C-X4-C-X9-C-X9-C-C) and β-defensins (C-X6-C-X4-C-X9-C-X6-C-C).

Cell and Tissue Specimens

Midgestation human fetal lung explants and adult gingival keratinocytes were cultured as reported previously (McCray et al., 1992; Mathews et. al., 1999). Specimens from skin, esophagus, trachea and placenta were obtained from donor tissues or from surgical samples. The study was approved by the Institutional Review Board at the University of Iowa.

Isolation of the CDNA for a Novel β-defensin, Human β-defensin-3 (HBD-3)

Human fetal lung explants were cultured in serum-free Waymouth's medium for 24 h with or without 100 ng/ml IL-1β (R & D Systems, Minneapolis, Minn.) (McCray et al.,1992). RNA was isolated from the explants and reverse transcribed to cDNA as previously described (McCray and Bentley, 1997). Primers were designed to flank the full-length open reading frame for the HBD-3 CDNA, based on the putative exon sequence determined from the BAC sequences. RT-PCR was conducted using the following oligonucleotide primers: forward: 5'-ATGAGGATCCATTATCTFCT-3'(SEQ ID NO: 5); reverse: 5'-TTATTTCTTTCTTCGGCAGC-3'(SEQ ID NO: 6). The first three nucleotides for each primer corresponds to the predicted start and stop codons, respectively. Each reaction contained approximately 1.25 pM of the primers, 3 mM $Mg^{2+}$ and 1 μl of the RT reaction product for a total volume of 20 ml. An initial denaturing step (95° C. for 3 min), was followed by 30 cycles of denaturing (94° C. for 30 s), annealing (60° C. for 30 s), and extending (72° C. for 30 s), followed by 5 min at 72° C. for elongation. The PCR product was cloned into the pBacPAK8 vector (Clontech, Palo Alto, Calif.) and transformed into DH5α E. coli. Several positive colonies were selected and purified plasmid DNA was sequenced to confirm the HBD-3 cDNA sequence. Sequence ambiguities were resolved with the program Sequencher (Gene Codes Corporation)

Tissue Distribution of HBD-3 mRNA

PCR was used to screen for HBD-3 mRNA expression in several tissues. Sample cDNA was purchased or generated from 1 μg of total RNA from each sample by reverse transcription using random hexamer primers according to manufacturer's instructions (SuperScript transcription system, GibcoBRL). For screening analysis, a commercial cDNA panel of fetal and adult tissues was tested (human multiple tissue cDNA, Cat. # K14220-1 and human fetal multiple tissue cDNA, Cat. # K1425-1, Clontech, Palo Alto, Calif.). Further tissue specific studies were performed using RNA samples isolated from skin, an esophageal biopsy, primary cultures of gingival keratinocytes (Mathews et al., 1999), autopsy trachea (McCray and Bentley, 1997), and placental membranes. Additional specific oligonucleotide primer sets were designed to the HBD-3 sequence and used for tissue distribution studies. The HBD-3 primers used were: forward: 5'-TGTTTGCTTTGCTCTTCCTG-3'(SEQ ID NO: 7); reverse: 5'-CTTTCT-TCGGCAGCATTTTC-3' (SEQ ID NO: 8). The predicted PCR product size was 179 bp. Each reaction contained approximately 1.25 pM of the primers, 3 mM $Mg^{2+}$, and 1 ml of the RT reaction product for a total volume of 20 ml. An initial denaturing step (95° C. for 3 min), was followed by 30 cycles of denaturing (94° C. for 30 s), annealing (60° C. for 30 s), and extending (72° C. for 30 s), followed by 5 min at 72° C. for elongation. The PCR products were separated by electrophoresis on a 2% agarose gel and visualized with ethidium bromide. As an internal control, GAPDH was also amplified in the reactions using the following primers: forward: 5'-GTCAGTGGTGGACCTGACCT-3' (SEQ ID NO: 9); reverse: 5'-AGGGGTCTACATGGCAACTG-3' (SEQ ID NO: 10). In selected specimens the specificity of the PCR amplification was confirmed by hybridization using a radiolabeled HBD-3 cDNA probe. RT-PCR products were separated on a 1.5% agarose gel, denatured in 0.5 N NaOH for 1 h and then transferred to a nylon membrane (Hybond-N+, Amersham) in 5 M NaCl and 0.5 N NaOH. The DNA was fixed to the membrane using an UV crosslinker and incubated in a prehybridization solution (high efficiency hybridization system, MRC) at 42° C. for 4 h. A HBD-3 fragment subcloned into the pBAK Pac8 vector (Clontech, Palo Alto, Calif.) was eluted and denatured, followed by $^{32}P$-dCTP labeling (Ready to Go DNA labeling Beads, Pharmacia Biotech). Hybridization was conducted at 42° C. for 18 h in the same solution used for prehybridization. The blot was washed three times with 6×SSC/0.5% SDS at room temperature and then three times with 1×SSC/0.5% SDS at 42° C. The hybridization signal was visualized by autoradiography using lot Kodak X-OMAT film (Eastern Kodak, Rochester, N.Y.) with intensifying screens at 80° C.

Figure 2:
FIG. 2: RT-PCR analysis of expression showing HBD-3 mRNA expression in esophagus, fetal lung following IL-1 stimulation, adult trachea, placenta, and gingiva.
Figure 2:
Figure 2:
Figure 2:

As shown in FIG. 1, PCR analysis of two commercial cDNA panels revealed HBD-3 mRNA expression in adult heart, skeletal muscle, and placenta, and in fetal thymus. HBD-3 expression in the placental sample was confirmed by isolating and sequencing the PCR product (data not shown). In another screening, an RNA dot blot (Multiple tissue expression array #7775-1, Clontech) was probed with the partial HBD-3 cDNA. The mRNA signal was most readily detected in esophagus (data not shown). Further tissue specific RT-PCR studies were performed to determine sites of HBD-3 expression. Based on the data from the screening studies and the inventors' previous studies of β-defensin expression in pulmonary and oral mucosal sites, RNA was isolated from skin, placental membranes, esophagus, and trachea. HBD-3 expression was readily detected in each of these tissues (FIG. 2). The specificity of the PCR amplification was verified by hybridization using an HBD-3 cDNA probe in the trachea and gingival epithelium specimens (not shown). Furthermore, in fetal lung explants and cultured gingival keratinocytes, HBD-3 mRNA expression increased markedly following treatment with 100 ng/ml IL-1β for 24 h. The PCR product generated from the IL-1β treated lung tissue explants was also isolated and sequenced to confirm that the product was indeed HBD-3 (SEQ ID NO: 1).

Identification of β-defensin Motifs in Members of the HE2 Gene Family

The HE2 gene on the β-defensin BAC contig. were identified by sequence analysis. The HE2 gene consists of six alternatively spliced products from a single locus (Hamil et al., 2000). Our defensin homology searches identified that the HE2β1 sequence encodes a β-defensin motif. The intron-exon boundaries of the HE2 gene locus were investigated by aligning the published HE2 mRNA sequences (Hamil et al., 2000) on the contig using the Sequencher program. In addition, PCR primer sets (Forward: 5'-TCGGAGAACTCAGGGAAAGA-3')(SEQ ID NO: 11), Reverse: (5'-GCCCTTGGGATACTTCAACA-3')(SEQ ID NO: 12) were designed to investigate the tissue expression patterns of HE2α1 and HE2β1. These primer sets generated products of 417 bp for HE2α1 and 341 bp for HE2β1. Bach reaction contained approximately 1.25 pM of the primers, 3 mM Mg$^{2+}$, and 1 μl of the RT reaction product for a total volume of 20 μl. An initial denaturing step (95° C. for 3 min), was followed by 35 cycles of denaturing (94° C. for 30 s), annealing (57° C. for 30 s), and extending (72° C. for 30 s), followed by 5 min at 72° C. for elongation. The PCR products were separated by electrophoresis on a 2% agarose gel and visualized with ethidium bromide.

Example 2
Identification of BAC Clones that Contain the HBD-2 Gene

Figure 3:
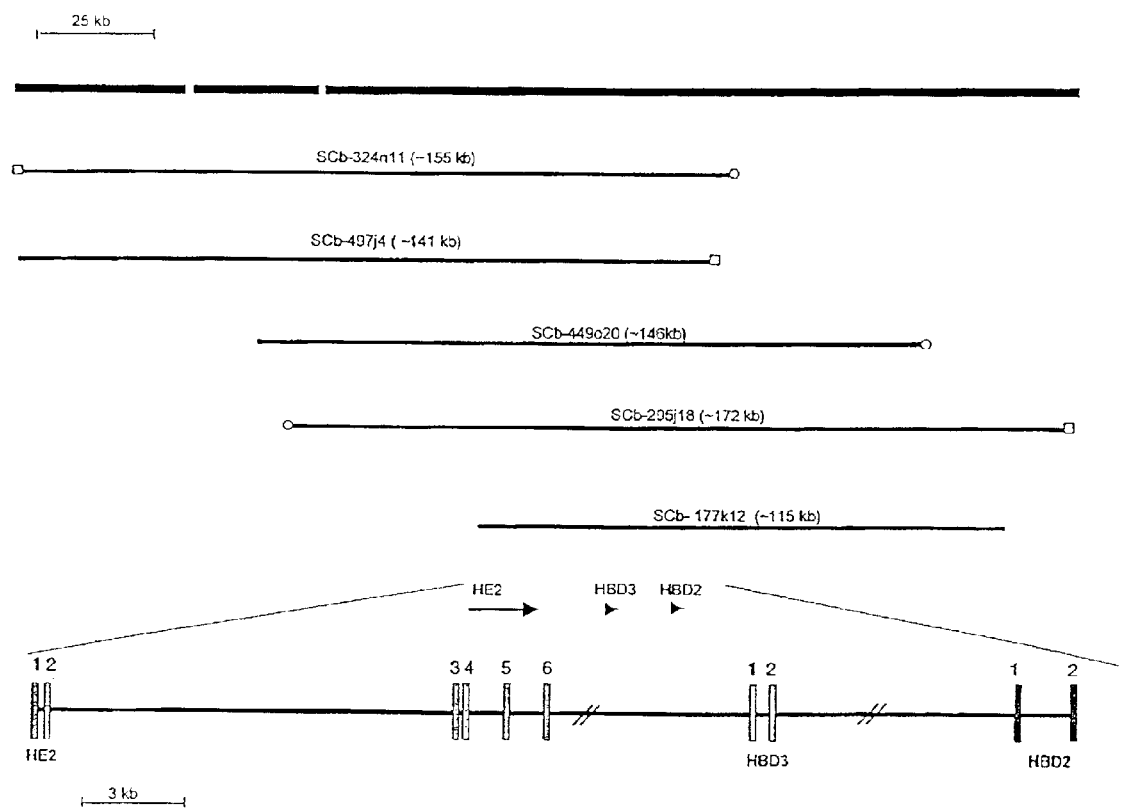
FIG. 3: BAC clones derived from the human β-defensin gene locus containing HBD-2. Five clones positive for HBD-2 by PCR screening were sequenced and aligned to construct a ~234 kb contig (see examples). The top thick line is the consensus sequence indicating two small gaps in the contig. The top left scale bar serves as a reference for this sequence. Below this each individual BAC clone and its length are noted. The T7 (open box) and SP6 (open circle) ends of the BACs are also noted. The bottom panel shows the relative orientation of coding regions for HBD-2 (dark rectangle), HBD-3 (open rectangle) and the HE2 (gray rectangle) genes and the directions of their transcription along the contig. The lower left scale bar serves as a reference to the bottom sequence.

The BAC library screening identified 5 clones positive for HBD-2 and a 'working draft' sequence was generated for them (Table 10). When the sequences for each of the 5 clones were aligned, the consensus sequence was divided into three contigs which spanned approximately 234 kb (FIG. 3). A similarity search identified several sequences from each clone with high homology to HBD-2. The sequences with highest homology were nearly identical to the previously published sequences for HBD-2 (Harder et al., 1997b; Liu et al., 1998). The only differences observed in the exons were a C to T silent substitution at position 84 from the ATG in the coding sequence and a C to T mutation at position 239 in the 30 UTR. These results prove that the HBD-2 gene is located in these clones and suggests the presence of two single nucleotide polymorphisms in this gene.

TABLE 10

STATUS OF SEQUENCE FROM BAC CLONES THAT CONTAIN THE HBD-2 GENE

| BAC Clone | GenBank acc. No. | Coverage | Contigs | Length (kb) |
|---|---|---|---|---|
| SCb-177k12 | AF252831 | 5.2 | 1 | ~115 |
| SCb-295j18 | AF252830 | 6.9 | 4 | ~172 |
| SCb-324n11 | AF189745 | 5.3 | 7 | ~155 |
| SCb-449o20 | AF285443 | 3.6 | 3 | ~146 |
| SCb-497j4 | AF202031 | 3.4 | 10 | ~141 |

Identification of a Novel β-defensin Gene, HBD-3

Figure 4:
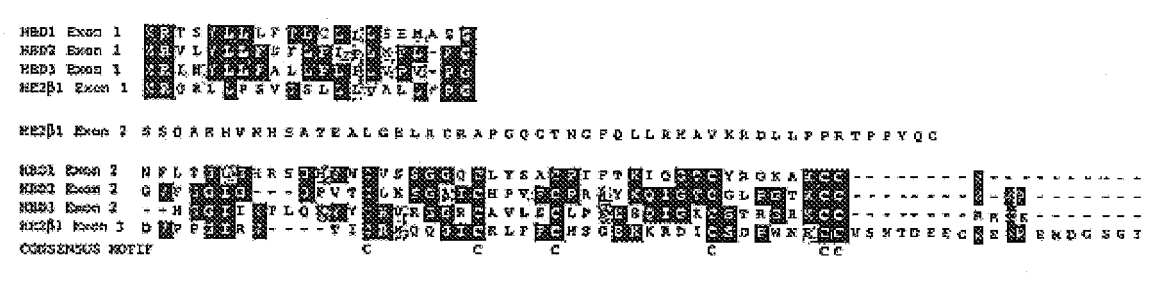

In addition to HBD-2, the similarity search also identified two other sequences that are predicted to encode peptides consistent with a β-defensin gene (FIG. 3). The first sequence was identical to the cDNA sequence for the previously cloned HE2 gene and the second was a novel gene that we designated human β-defensin-3 (HBD-3). HBD-3 is located, 13 kb upstream from the HBD-2 gene and HE2 is located another 17 kb farther upstream. All three of these genes are transcribed in the same direction (FIG. 3). The intron exon boundaries for these genes are shown in Table 11. To confirm that the HBD-3 gene predicted by the analysis of the genomic sequence was expressed, mRNA analysis was performed. Since the expression of β-defensins can be inducible (Singh et al., 1998; Mathews et al., 1999), screening for expression in a human lung tissue model was carried out in the presence or absence of pro-inflammatory stimuli. As shown in SEQ ID NO: 1 a partial cDNA clone containing only the HBD-3 open reading frame was PCR amplified from cDNA derived from IL-1β stimulated human fetal lung tissue. The sequence of the 204 bp PCR product (GenBank accession no. AF217245) contained a single open reading frame that encodes a 67 amino acid peptide that is 43% identical to HBD-2 and faithfully shares the cysteine motif of the β-defensins (FIG. 4). This partial cDNA sequence was identical to the genomic sequence except for a 943 bp intervening sequence. Consensus splice sites are located at the ends of the intervening sequence demonstrating that it is an intron. These data demonstrate that HBD-3 is a real gene that consists of at least two exons (Table 11). No HBD-3 signal was detected from the midgestation lung tissue that was cultured in the absence of IL-1β (see below), suggesting that HBD-3 gene expression may be inducible. For other inducible defensins, NFkB consensus elements were reported near the gene (Harder et al, 1997; Liu et al.,1998). In this case, no NFkB consensus elements were observed in 2900 bp of sequence 50 to the HBD-3 coding.

TABLE 11

Exon/intron boundaries for the introns of the HBD-3 and HE2 genes. Exon sequence in indicated in upper case, introl sequence is in lower case. The numbers in the position column indicate the number of bases from the A nucleotide of the ATG start codon of the HBD-3 or HE2 cDNA sequences.

| Intron | Position | 5'—3' Sequence at EXON/intron boundary | |
|---|---|---|---|
| HBD3 | | | |
| I | 58–59 | TGTTCCAGgtaagatgggctgggaaatc SEQ ID NO. 13 | GtgctgttttgtcattgcagGTCATGGA SEQ ID NO. 14 |
| HE2 | | | |
| I | 61–62 | GTTTCCAGgtaaaatggaaaggtgaccc SED IQ NO. 15 | GtgtgtttccacttgcacagGATCGTCT SED IQ NO. 16 |

TABLE 11-continued

Exon/intron boundaries for the introns of the HBD-3 and HE2 genes.
Exon sequence in indicated in upper case, introl sequence is in
lower case. The numbers in the position column indicate the
number of bases from the A nucleotide of the ATG start
codon of the HBD-3 or HE2 cDNA sequences.

| Intron | Position | 5'–3' Sequence at EXON/intron boundary | |
|---|---|---|---|
| II | 214–215 | TTACCAAGgtgagtcagggaccaacacg<br>SED IQ NO. 17 | CtcccttttgtttccttctagTGCACATC<br>SED IQ NO. 18 |
| III | 290–291 | TGGGCCAGgtgagcattcataaaacaca<br>SED IQ NO. 19 | CtcttctgttgtatccatagGGGATGTT<br>SED IQ NO. 20 |
| IV | 575–576 | CCATTCTGgtgagaaaaagcgtgacatt<br>SED IQ NO. 21 | TttggcctcatgttcctcagAAATGAAA<br>SED IQ NO. 22 |
| V | 679–680 | TCCACCAGgtgagatgggaggatggga<br>SED IQ NO. 23 | CtgctcttatttgggaacagGGACAGGC<br>SED IQ NO. 24 |

Identification of the HE2 Gene Locus in the Defensin Gene Cluster

Figure 5:
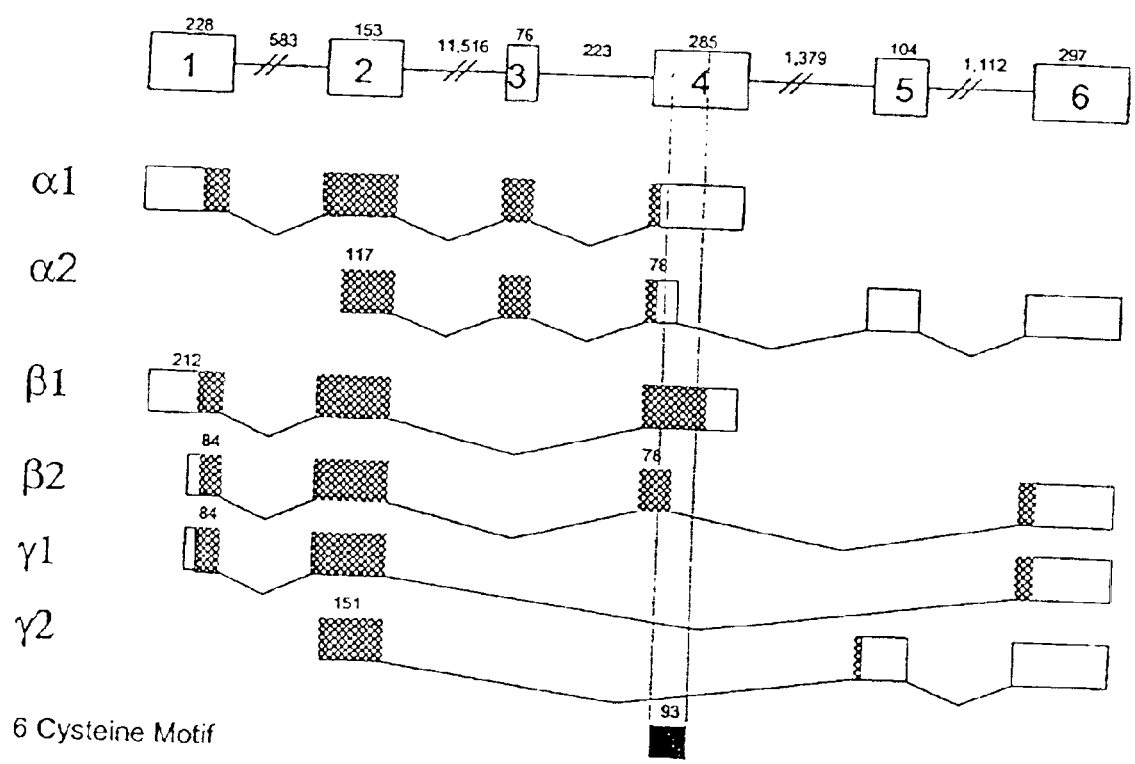
FIG. 5. Genomic organization of the HE2 gene locus. The exons were determined by aligning the published cDNA sequence (Hamil et al., 2000) along the genomic contig. Each of the six HE2 trancripts is derived from the alternative splicing of six exons. HE2β1 is a three exon gene product and contains a β-defensin six cysteine motif. The upper panel indicates the alignment of the six exons with their respective exon and intron sizes in nucleotides indicated. For each trancript, the white box indicates untranslated sequence, the gray box indicates coding sequence. The black box at the bottom indicates the location of the six cysteine defensin motif.

Further analysis of the BAC clone sequences identified an additional gene containing a β-defensin peptide motif A sequence similarity search with this sequence revealed regions that were identical to the previously identified gene HE2 (human epididymal secretory protein) (Kirchhoff et al., 1990; Krull et al., 1993; Osterhoff et al., 1994; Hamil et al., 2000). The HE2 gene produces six mRNA products (HE2α1, HE2α2, HE2β1, HE2β2, HE2γ1, and HE2γ2) by alternative splicing (Hamil et al., 2000). When aligned with the genomic sequences, these products were divided into six exons (Table 2). The sequence containing the β-defensin motif is located in exon 4 (FIG. 5). Of the six known splice variants, only the predicted protein sequence for HE2β1 contains this motif (FIG. 4). Outside of this region, the HE2β1 gene product shows little homology to the β-defensins and it is larger, containing more amino acids in the middle of the protein and at the C-terminus, than other β-defensins. The HE2 gene consists of six exons (Hamil et al., 2000), and the fourth exon of the HE locus is a 285 nucleotide cassette encoding the β-defensin six cysteine sequence (Tables 10 and 11, FIG. 5). In contrast to HBD-1, -2 and -3, HE2β1 is a three exon gene with the second exon encoding sequence with no β-defensin homology and the location of the intervening sequences for HE2β1 does not resemble the β-defensin genes (FIG. 4). The HE2α1 gene also contains the sequence that encodes the six cysteine motif, but it resides in the 3' untranslated region of the gene (FIG. 5).

HE2β1 MRNA Expression in Tissues Outside the Epididymis

Limited RT-PCR analysis for HE2β1 expression was carried out using RNA derived from primary cultures of gingival keratinocytes and bronchial epithelia. A primer set was designed that included a forward primer from exon 2 and a reverse primer from exon 4 of HE2 (see Example 1). Appropriate sized PCR products were amplified from both samples. These products were confirmed to be HE2α1 and HE2β1 by sequencing.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,817,837
U.S. Pat. No. 3,850,752
U.S. Pat. No. 3,850,752
U.S. Pat. No. 3,939,350
U.S. Pat. No. 3,996,345
U.S. Pat. No. 3,996,345
U.S. Pat. No. 4,196,265
U.S. Pat. No. 4,275,149
U.S. Pat. No. 4,275,149
U.S. Pat. No. 4,277,437
U.S. Pat. No. 4,277,437
U.S. Pat. No. 4,366,241
U.S. Pat. No. 4,366,241
U.S. Pat. No. 4,472,509
U.S. Pat. No. 4,472,509
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,202
U.S. Pat. No. 4,797,368
U.S. Pat. No. 4,879,236
U.S. Pat. No. 4,938,948
U.S. Pat. No. 4,938,948
U.S. Pat. No. 5,021,236
U.S. Pat. No. 5,139,941
U.S. Pat. No. 5,196,066
U.S. Pat. No. 5,871,986
U.S. Pat. No. 5,925,565
U.S. Pat. No. 5,928,906
U.S. Pat. No. 5,935,819
U.S. Pat. No. 3,939,350

Abbondanzo, *Ann Diagn Pathol*, 3(5):318–27, 1999.
Almendro et al., *J Immunol*, 157(12):5411–5421, 1996.
Angel et al., *Cell*, 49:729, 1987b.
Angel et al., *Mol. Cell. Biol.*, 7:2256, 1987a.
Antibodies: *A Laboratory Manual*, Cold Spring Harbor Laboratory, 1985.
Atherton et al., *Biol Reprod*, 32(1):155–171, 1985.
Baichwal and Sugden, In: *Gene Transfer*, Kucherlapati (ed.), New York, Plenum Press, 117–148, 1986.
Banedji et al., *Cell*, 27:299, 1981.
Banerji et al., *Cell*, 35:729, 1983.
Berberian et al., *Science*, 261(5128):1588–91, 1993.
Berkhout et al., *Cell*, 59:273, 1989.
Berklman et al., *J. Infect Dis.*, 170(2):272–7, 1994.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5:1615, 1986.
Braddock et al., *Cell*, 58:269, 1989.
Bulla and Siddiqui, *J. Virol.*, 62:1437, 1986.
Campbell and Villarreal, *Mol. Cell. Biol.*, 8:1993, 1988.
Campbell et al., *Am Rev Respir Dis*, 130(3):417–23, 1984.
Campere and Tilghman, *Genes and Dev.*, 3:537, 1989.
Campo et al., *Nature*, 303:77, 1983.
Carbonelli et al., *FEMS Microbiol Lett*, 177(1):75–82, 1999.
Celander and Haseltine, *J. Virology*, 61:269, 1987.
Celander et al., *J. Virology*, 62:1314, 1988.
Chandler et al., *Proc Natl Acad Sci USA*, 94(8):3596–3601, 1997.
Chandler et al., *Cell*, 33:489, 1983.
Chang et al., 14:124A, 1991.
Chang et al., Hepatology, 14:124A, 1991.
Chatterjee et al., *Proc. Nat'l Acad. Sci. USA*, 86:9114, 1989.
Chen and Okayama, Mol. Cell Biol., 7:2745–2752, 1987.
Choi et al., *Cell*, 53:519, 1988.
Clark et al.,*Hum Gene Ther*, 6(10):1329–41, 1995.
Cleary et al., *J Biol Chem*, 269(29):18747–9, 1994.
Cleeland and Squires, In: Lorian, Antibiotics in Laboratory Medicine, Satterfield (Ed), Williams & Wilkins, Philadelphia, 1991.
Cocea, *Biotechniques*, 23(5):814–6, 1997.
Coffin, In: Fields B N, Knipe D M, ed. Virology. New York: Raven Press, pp. 1437–1500, 1990.
Cohen et al., *J. Cell. Physiol.*, 5:75, 1987.
Costa et al., *Mol. Cell. Biol.*, 8:81, 1988.
Cotton et al., *Proc Natl Acad Sci USA*, 89(13):6094–8, 1992.
Couch et al., Am. Rev. Resp. Dis., 88:394–403, 1963.
Coupar et al., Gene, 68:1–10, 1988.
Cripe et al., *EMBO J.*, 6:3745, 1987.
Culotta and Hamer, *Mol. Cell. Biol.*, 9:1376, 1989.
Curiel, *Nat Immun*, 13(2–3):141–64, 1994.
Dandolo et al., *J. Virology*, 47:55, 1983.
Davies, FEMS Microbiology Reviews, 39:363–371, 1986.
De Jager et al., *Semin Nucl Med*, 23(2):165–79, 1993.
De Villiers et al., *Nature*, 312:242, 1984.
Deschamps et al., *Science*, 230:1174, 1985.
Dholakia et al., 1989, *J Biol Chem*, 264(34):20638–42, 1989.
Doolittle and Ben-Zeev, *Methods Mol Biol*, 109:215–37, 1999.
Edbrooke et al., *Mol. Cell. Biol.*, 9–1908, 1989.
Edlund et al., *Science*, 230:912, 1985.
EPO 0273085
Fechheimer et al., Proc. Nat'l. Acad. Sci. USA, 84:8463–8467, 1987.
Feng and Holland, *Nature*, 334:6178, 1988.
Firak and Subramanian, *Mol. Cell. Biol.*, 6:3667, 1986.
Flotte et al., *Am J Respir Cell Mol Biol*, 7(3):349–356, 1992.
Flotte et al., *Gene Ther*, 2(1):29–37, 1995.
Flotte et al., *Proc Natl Acad Sci USA*, 90(22):10613–7, 1993.
Foecking and Hofstetter, *Gene*, 45:101, 1986.
Fraley et al., Proc. Nat'l Acad. Sci. USA, 76:3348–3352, 1979.
Friedmann, Science, 244:1275–1281, 1989.
Fujita et al., *Cell*, 49:357, 1987.
Gallo et al., J. Biol. Chem., 272:13088–13093, 1997.
Gallo et al., J Invest Dermatol., 111(5):739–43, 1998.
Ganz and Lehrer, Current Opinions Immun,. 10:41, 1998.
Gefter et al., *Somatic Cell Genet*, 3(2):231–6, 1977.
Ghosh and Bachhawat, In: Wu G. and C. Wu (eds.) Liver diseases, targeted diagnosis and therapy using specific receptors and ligands, New York: Marcel Dekker, pp. 87–104, 1991.
Ghosh-Choudhury et al., EMBO J., 6:1733–1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., J. Biol. Chem., 267:25129–25134, 1992.
Goodbourn and Maniatis, *Proc. Nat'l Acad. Sci. USA*, 85:1447, 1988.
Goodbourn et al., *Cell*, 45:601, 1986.
Gopal, Mol. Cell Biol., 5:1188–1190, 1985.
Graham and Prevec, Biotechnology, 20:363–390, 1992.
Graham and Prevec, In: E. J. Murray (ed.), Methods in Molecular Biology: Gene Transfer and Expression Protocol, Clifton, N.J.: Humana Press, 7:109–128, 1991.
Graham et al., J. Gen. Virol., 36:59–72, 1977.
Greene et al., *Immunology Today*, 10:272, 1989.
Grosschedl and Baltimore, *Cell*, 41:885, 1985.
Grunhaus and Horwitz, *Seminar in Virology*, 3:237–252, 1992.
Gulbis and Galand, *Hum Pathol*, 24(12):1271–85, 1993.
Hamil et al., *Endocrinology*, 141(3):1245–53, 2000.
Harder et al., *Genomics*, 46(3):472–5, 1997.
Harland and Weintraub, J. Cell Biol., 101:1094–1099, 1985.
Haslinger and Karin, *Proc. Nat'l Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Nat'l Acad. Sci. USA*, 81:6466–6470, 1984.
Herr and Clarke, *Cell*, 45:461, 1986.
Hersdorffer et al., DNA Cell Biol., 9:713–723, 1990.
Herz and Gerard, Proc. Nat'l Acad. Sci. USA, 90:2812–2816, 1993.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Horwich, et al., J. Virol., 64:642–650, 1990.
Huang et al., *Cell*, 27:245, 1981.
Hug et al., *Mol. Cell Biol.* 1988 Aug;8(8):3065–79.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Shenk, Cell, 13:181–188, 1978.
Kadesch and Berg, *Mol. Cell. Biol.*, 6:2593, 1986.

Kang et al., *Science*, 240(4855):1034–6, 1988.
Karin et al., *Mol. Cell. Biol.*, 7:606, 1987.
Karin et al., *Mol. Cell. Biol.*, 7:606, 1987.
Karlsson et al., EMBO J., 5:2377–2385, 1986.
Kasahara et al., *Science*, 266(5189):1373–6, 1994.
Katinka et al., *Cell*, 20:393, 1980.
Katinka et al., *Cell*, 20:393, 1980.
Katinka et al., *Nature*, 290:720, 1981.
Katinka et al., *Nature*, 290:720, 1981.
Kato et al., J. Biochem. Tokyo, 101:207–215, 1987.
Kawamoto et al., *Mol. Cell. Biol.*, 8:267, 1988.
Kawamoto et al., *Mol. Cell. Biol.*, 8:267, 1988.
Kelleher and Vos, *Biotechniques*, 17(6):1110–7, 1994.
Khatoon et al., *Ann Neurol*, 26(2):210–5, 1989.
Kiledjian et al., *Mol. Cell. Biol.*, 8:145, 1988.
Kiledjian et al., *Mol. Cell. Biol.*, 8:145, 1988.
King et al., *J Biol Chem*, 264(17):10210–10218, 1989.
Kirchhoff et al., *Mol Reprod Dev*, 56(1):26–33, 2000.
Klaassen, In: The Pharnacological Basis of Therapeutics, Goodman and Gilman, Eds., Pergamon Press, 8th Ed., pp. 49–61, 1990.
Klamut et al., *Mol. Cell. Biol.*, 10:193, 1990.
Klamut et al., *Mol. Cell. Biol.*, 10:193, 1990.
Klein et al., *Nature*, 327:70–73, 1987.
Koch et al., *Mol. Cell. Biol.*, 9:303, 1989.
Koch et al., *Mol. Cell. Biol.*, 9:303, 1989.
Kohler and Milstein, *Eur J Immunol*, 6(7):511–9, 1976.
Kohler and Milstein, *Nature*, 256(5517):495–7, 1975.
Kohler et al., *Methods Enzymol*, 178:3–35, 1989.
Kotin et al., *Proc Natl Acad Sci USA*, 1990 Mar;87(6): 2211–5, 1990.
Kraus et al., *FEBS Lett* 428(3): 165–70, 1998.
Kraus et al., *FEBS Lett*, 428(3):165–170, 1998.
Kriegler and Botchan, In: *Eukaryotic Viral Vectors*, Y. Gluzman, ed., Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kriegler et al., In: *Gene Expression*, Hamer and Rosenberg, eds., New York: 1983.
Krull et al., *Mol Reprod Dev*, 34(1):16–24, 1993.
Kuhl et al., *Cell*, 50:1057, 1987.
Kunz et al., *Nucl. Acids Res.*, 17:1121, 1989.
Kyte and Doolittle, *J Mol Biol*, 157(1):105–32, 1982.
LaFace et al., *Virology*, 162(2):483–6, 1988.
Lareyre et al., *J Biol Chem*, 274(12):8282–90, 1999.
Larsen et al., *Proc. Nat'l Acad. Sci. USA*, 83:8283, 1986.
Laspia et al., *Cell*, 59:283, 1989.
Latimer et al., *Mol. Cell. Biol.*, 10:760, 1990.
Laughlin et al., *J Virol*, 60(2):515–24, 1986.
Le Gal La Salle et al., *Science*, 259:988–990, 1993.
Lebkowski et al., *Mol Cell Biol*, 8(10):3988–96, 1988.
Lee et al., *DNA Cell Biol*, 16(11):1267–1275, 1997.
Lenert et al., *Science*, 248(4963):1639–43, 1990.
Levenson et al., *Hum Gene Ther*, 9(8):1233–6, 1998.
Levinson et al., *Nature*, 295:79, 1982.
Levrero et al., *Gene*, 101:195–202, 1991.
Lin et al., *Mol. Cell. Biol.*, 10:850, 1990.
Liu et al., Mol *Carcinog*, 22(4):23546, 1998.
Lorian, In: Antibiotics in Laboratory Medicine, Satterfield (Ed), Williams and Wilkins, Philadelphia, pp. 558–559;718, 1991.
Luria et al., *EMBO J.*, 6:3307, 1987.
Lusky and Botchan, *Proc. Nat'l Acad. Sci. USA*, 83:3609, 1986.
Lusky et al., *Mol. Cell. Biol.*, 3:1108, 1983.
Macejak and Sarnow, Nature, 353:90–94, 1991.
Majors and Varmus, *Proc. Nat'l Acad. Sci. USA*, 80:5866, 1983.
Mann et al., *Cell*, 33:153–159, 1983.
Markowitz et al., *J. Virol.*, 62:1120–1124, 1988.
Mathews et al., *Infect Immun*, 67(6):2740–5, 1999.
McCarty et al., *J Virol*, 65(6):2936–45, 1991.
McCray Jr et al., *J Clin Invest*, 90(2):619–25, 1992.
McLaughlin et al., *J Virol*, 62(6):1963–73, 1988.
McNeall et al., *Gene*, 76:81, 1989.
Miksicek et al., *Cell*, 46:203, 1986.
Miller et al., *Am J Clin Oncol*, 15(3):216–21, 1992.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Muzyczka, *Curr Top Microbiol Immunol*, 158:97–129, 1992.
Ng et al., *Nuc. Acids Res.*, 17:601, 1989.
Nicolas and Rubenstein, In: *Vectors: A survey of molecular cloning vectors and their uses*, Rodriguez and Denhardt (eds.), Stoneham: Butterworth, pp. 494–513, 1988.
Nicolau and Sene, Biochem. Biophys. Acta, 721:185–190, 1982.
Nicolau et al., Methods Enzymol., 149:157–176, 1987.
Nilsson, Klang, Berg, *Dermatol Nurs*, 11(2):117–22, 1999.
Nomoto et al., *Gene*, 236(2):259–71, 1999.
O'Shannessy et al., *Anal Biochem*, 163(1):204–209, 1987.
Ohi et al., Gene, 89(2):279–282, 1990.
Omnitz et al., *Mol. Cell. Biol.*, 7:3466, 1987.
Ondek et at, *EMBO J.*, 6:1017, 1987.
Oren et al., *Biopolymers*, 47(6):451–63, 1998.
Osterhoff et al., *Biol Reprod*, 50(3):516–25, 1994.
Ostreicher, NY State Dent. J., 60(3):47–49, 1994.
Owens and Hardy, *Biochem Biophys Res Commun*, 142(3): 964–71, 1987.
Palmiter et al., *Nature*, 300:611, 1982.
Paskind et al., Virology, 67:242–248, 1975.
Pech et al., *Mol. Cell. Biol.*, 9:396, 1989.
Pelletier and Sonenberg, Nature, 334:320–325, 1988.
Perales et al., Proc. Nat'l Acad. Sci., 91:4086–4090, 1994.
Perez-Stable and Constantini, *Mol. Cell. Biol.*, 10:1116, 1990.
Picard and Schaffner, Nature, 307:83, 1984.
Pinkert et al., *Genes and Dev.*, 1:268, 1987.
Ponta et al., *Proc. Nat'l Acad. Sci. USA*, 82:1020, 1985.
Porton et al., *Mol. Cell. Biol.*, 10:1076, 1990.
Potter and Haley, *Methods Enzymol*, 91:613–633, 1983.
Potter et al., Proc. Nat'l Acad. Sci. USA, 81:7161–7165, 1984.
Queen and Baltimore, *Cell*, 35:741, 1983.
Quinn et al., *Mol. Cell. Biol.*, 9:4713, 1989.
Racher et al., Biotechnology Techniques, 9:169–174, 1995.
Ragot et al., Nature, 361:647–650, 1993.
Redondo et al., *Science*, 247:1225, 1990.
Reese and Betts, In: A Practical Approach to Infectious Diseases, (3rd ed.), Boston, Little Brown, 1991.
Reisman and Rotter, *Mol. Cell. Biol.*, 9:3571, 1989.
Remington's Pharmaceutical Sciences, 15th Edition, Chapter 61, pages 1035–1038 and 1570–1580.
Resendez Jr. et al., *Mol. Cell. Biol.*, 8:4579, 1988.
Rich et al., Hum. Gene Ther., 4:461–476, 1993.
Ridgeway, In: Rodriguez R L, Denhardt D T, ed. Vectors: A survey of molecular cloning vectors and their uses, Stoneham: Butterworth, pp. 467–492, 1988.

Ripe et al., *Mol. Cell. Biol.*, 9:2224, 1989.
Rippe et al., *Mol. Cell Biol.*, 10:689–695, 1990.
Rittling et al., *Nucl. Acids Res.*, 17:1619, 1989.
Rosen et al., *Cell 41:813*, 1988.
Rosenfeld et al., Cell, 68:143–155, 1992.
Rosenfeld et al., Science, 252:431–434, 1991.
Roux et al., Proc. Nat'l Acad. Sci. USA, 86:9079–9083, 1989.
Russel et al., *Infect Immun*, 64(5):15 65–8, 1996.
Sambrook, Fritsch, Maniatis, *Molecular Cloning: A Laboratory Manual*, 2nd Ed., Cold Spring Harbor Press, Cold Spring Harbor, N.Y., 1989.
Samulski et al, *EMBO J*, 10:3941–3950, 1991.
Samulski et al., *J. Virol*, 63:3822–3828, 1989.
Sasso et al., *J. Immunol.*, 142:2778–2783, 1989.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Shelling and Smith, *Gene Therapy*, 1:165–169, 1994.
Sheppard et al., Journal of Chemical Society, p.538, 1981.
Sherman et al., *Mol. Cell. Biol.*, 9:50, 1989.
Shorki et al., *J. Immunol.*, 146:936–940, 1991.
Silvermann et al., *J. Clin. Invest.*, 96:417–426, 1995.
Singh et al., *Proc Natl Acad Sci USA*, 95(25):14961–6, 1998.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Stratford-Perricaudet and Perricaudet, In: Human Gene Transfer, Eds, O. Cohen-Haguenauer and M. Boiron, Editions John Libbey Eurotext, France, pp. 51–61, 1991.
Stratford-Perricaudet et al., Hum. Gene Ther., 1:241–256, 1990.
Stuart et al., Nature, 317:828, 1985.
Sullivan and Peterlin, *Mol. Cell. Biol.*, 7:3315, 1987.
Swartzendruber and Lehman, *J. Cell. Physiology*, 85:179, 1975.
Szoka and Papahadjopoulos, Proc. Nat'l Acad. Sci. USA, 75: 4194–4198, 1978.
Takebe et al., *Mol. Cell. Biol.*, 8;466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: Gene Transfer, Kucherlapati (ed.), New York: Plenum Press, pp. 149–188, 1986.
Thiesen et al., *J. Virology*, 62:614, 1988.
Top et al., J. Infect. Dis., 124:155–160, 1971.
Tratschin,et al., *Mol. Cell. Biol.*, 4:2072–2081, 1984.
Travis, J., Science, 264(5157):360–2, 1994.
Treisman, *Cell*, 42:889, 1985.
Tronche et al., *Mol. Biol. Med.*, 7:173, 1990.
Trudel and Constantini, *Genes and Dev.* 6:954, 1987.
Tsumaki et al., *J. Biol Chem.*, 273(36):22861–22864, 1998.
Tur-Kaspa et al., Mol. Cell Biol., 6:716–718, 1986.
Tyndell et al., *Nuc. Acids. Res.*, 9:6231, 1981.
Vannice and Levinson, *J. Virology*, 62:1305, 1988.
Vasseur et al., *Proc. Nat'l Acad. Sci. USA.*, 77:1068, 1980.
Wagner et al., *Proc. Nat'l Acad. Sci. USA*, 87(9):3410–3414, 1990.
Walsh et al., *J. Clin. Invest*, 94:1440–1448, 1994.
Wang and Calame, *Cell*, 47:241, 1986.
Weber et al., *Cell*, 36:983, 1984.
Wei et al., *Gene Therapy*, 1:261–268, 1994.
Weinberger et al. *Mol. Cell. Biol.*, 8:988, 1984.
Winoto and Baltimore, *Cell* 59:649, 1989.
Wong et al., Gene, 10:87–94, 1980.
Wu & Wu, J. Biol. Chem., 262:4429–4432, 1987.
Wu and Wu, Adv. Drug Delivery Rev., 12:159–167, 1993.
Wu et al., *Biochem Biophys Res Commun.*, 233(1):221–226, 1997.
Yang et al., Proc. Nat'l Acad. Sci USA, 87:9568–9572, 1990
Yang et al., *Proc. Natl. Acad. Sci. USA*, 91:4407–4411, 1994.
Yang, et al. Science, 286:525–8, 1999.
Yoder et al., *Blood*, 82 (Supp.): 1:347A, 1994.
Yutzey et al., *Mol. Cell. Biol.*, 9:1397, 1989.
Zak and Sande, In: Action of Antibiotics in Patients, Sabath, Ed., Hans HuberZanetti et al., FEBS Lett., 374:1–5, 1995.
Zhao-Emonet et al., *Biochim Biophys Acta*, 1442(2–3): 109–119, 1998.
Zhou et al., *Exp. Hematol*, 21:928–933, 1993.
Zhou et al., *J.Exp.Med.*, 179:1867–1875, 1994.

---

What is claimed is:

1. An isolated antimicrobial peptide comprising the amino acid sequence of SEQ ID NO:2, wherein said antimicrobial peptide is contained in a pharmaceutical composition formulated for oral administration and wherein said pharmaceutical composition includes a pharmaceutically acceptable carrier.

2. A method of inhibiting growth of a microbe in a host comprising orally administering to said host an antimicrobial peptide comprising the amino acid sequence of SEQ ID NO:2, SEQ ID NO:3 or SEQ ID NO:4, wherein said antimicrobial peptide is contained in a pharmaceutical composition formulated for oral administration and wherein said pharmaceutical composition includes a pharmaceutically acceptable carrier.

3. The method of claim 2, further comprising administering an additional antimicrobial agent.

4. The method of claim 3, wherei said antimicrobial peptide is administered before said additional antimicrobial agent.

5. The method of claim 3, wherein said antimicrobial peptide and said additional antimicrobial agent are administered concurrently.

6. The method of claim 3, wherein said antimicrobial peptide is administered after said additional antimicrobial agent.

7. The method of claim 3, wherein said additional antimicrobial agent is selected from the group consisting of a protein synthesis inhibitor, a cell wall growth inhibitor, a cell membrane syntheis inhibitor, a nucleic acid synthesis inhibitor, and a competitive inhibitor.

8. An isolated antimicrobial peptide comprising the amino acid sequence of SEQ ID NO:3, wherein said antimicrobial peptide is contained in a pharmaceutical composition formulated for oral administration and wherein said pharmaceutical composition includes a pharmaceutically acceptable carrier.

9. The antimicrobial peptide of claim 8, wherein said antimicrobial peptide comprises the amino acid sequene: of SEQ ID NO: 4.

* * * * *

UNITED STATES PATENT AND TRADEMARK OFFICE
CERTIFICATE OF CORRECTION

PATENT NO. : 6,809,181 B2
DATED : October 26, 2004
INVENTOR(S) : McCray, Jr. et al.

It is certified that error appears in the above-identified patent and that said Letters Patent is hereby corrected as shown below:

Column 78,
Line 42, please delete "sequence:" and insert -- sequence --.

Signed and Sealed this

Nineteenth Day of April, 2005

JON W. DUDAS
*Director of the United States Patent and Trademark Office*